US008426400B2

(12) United States Patent
Koppel et al.

(10) Patent No.: US 8,426,400 B2
(45) Date of Patent: *Apr. 23, 2013

(54) β-LACTAMYL PHENYLALANINE, CYSTEINE, AND SERINE VASOPRESSIN ANTAGONISTS

(75) Inventors: Gary A. Koppel, Indianapolis, IN (US); Marvin J. Miller, South Bend, IN (US)

(73) Assignee: Azevan Pharmaceuticals, Inc., Bethlehem, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/285,590

(22) Filed: Oct. 31, 2011

(65) Prior Publication Data
US 2012/0220765 A1 Aug. 30, 2012

Related U.S. Application Data

(63) Continuation of application No. 11/996,006, filed as application No. PCT/US2006/027703 on Jul. 18, 2006, now Pat. No. 8,048, 874.

(60) Provisional application No. 60/700,673, filed on Jul. 19, 2005.

(51) Int. Cl.
C07D 205/085 (2006.01)
A61K 31/397 (2006.01)
C07D 403/04 (2006.01)
C07D 413/04 (2006.01)
A61P 25/22 (2006.01)

(52) U.S. Cl.
USPC .............. 514/210.02; 540/363; 540/364

(58) Field of Classification Search .......... 540/363, 540/364; 514/210.02
See application file for complete search history.

(56) References Cited

U.S. PATENT DOCUMENTS

| 3,912,743 A | 10/1975 | Christensen et al. |
| 4,007,196 A | 2/1977 | Christensen et al. |
| 4,085,225 A | 4/1978 | Welle et al. |
| 4,136,193 A | 1/1979 | Bogese et al. |
| 4,314,081 A | 2/1982 | Molloy et al. |
| 4,341,698 A | 7/1982 | Carr et al. |
| 4,352,752 A | 10/1982 | Ojima et al. |
| 4,478,836 A | 10/1984 | Mouzin et al. |
| 4,536,518 A | 8/1985 | Welch |
| 4,576,753 A | 3/1986 | Kamiya et al. |
| 4,734,498 A | 3/1988 | Cooper |
| 4,751,299 A | 6/1988 | Sugawara et al. |
| 4,761,501 A | 8/1988 | Husbands et al. |
| 4,772,694 A | 9/1988 | Cooper et al. |
| 4,956,388 A | 9/1990 | Robertson et al. |
| 5,011,472 A | 4/1991 | Aebischer et al. |
| 5,023,252 A | 6/1991 | Hseih |
| 5,759,865 A | 6/1998 | Bruns et al. |
| 6,204,260 B1 | 3/2001 | Bruns et al. |
| 6,403,632 B1 | 6/2002 | Duan et al. |
| 6,610,680 B1 | 8/2003 | Rizzo et al. |
| 6,627,625 B1 | 9/2003 | Koppel |
| 7,119,083 B2 | 10/2006 | Bruns et al. |
| 7,179,907 B2 | 2/2007 | Eaton et al. |
| 7,268,125 B2 | 9/2007 | Bruns et al. |
| 8,048,874 B2 * | 11/2011 | Koppel et al. ............ 514/210.02 |
| 2004/0132714 A1 | 7/2004 | Zhou et al. |
| 2005/0059650 A1 | 3/2005 | Jones et al. |
| 2006/0281728 A1 | 12/2006 | Guillon et al. |
| 2009/0170825 A1 | 7/2009 | Koppel et al. |
| 2010/0016274 A1 | 1/2010 | Koppel et al. |

FOREIGN PATENT DOCUMENTS

| EP | 0144840 | 6/1985 |
| EP | 0591040 | 9/1993 |
| JP | 56125361 | 10/1981 |
| WO | WO93/16609 | 6/1993 |
| WO | WO94/01402 | 1/1994 |
| WO | WO94/04494 | 3/1994 |
| WO | WO94/26735 | 11/1994 |
| WO | WO 97/30707 | 8/1997 |
| WO | WO97/30707 | 8/1997 |
| WO | WO02/12187 | 2/2002 |
| WO | WO 03/031407 | 4/2003 |
| WO | WO/03/031407 | 4/2003 |
| WO | WO/2006/102283 | 9/2006 |

OTHER PUBLICATIONS

Hakimelahi, "The Synthesis of Highly Strained Monocyclic and Bicyclic β-Lactams (delta-Carbapenem)," Helvetica Chimica Acta, 1982, 65 Fasc., pp. 1378-1384.
Hirai, Koichi, et al., "An Example of The β-Lactam Ring Rormation and Novel Pyrrolinoazetidinone Ring Construction," 1985, Sankyo Kenkyusho Nempo, vol. 37, pp. 133-139.
Ojima, Iwao, et al., "Novel and Effective Routes to Optically Pure Amino Acids, Dipeptides, and Their Derivatives Via β-Lactams Obtained Through Asymmetric Cycloaddition," 1987, J. Am. Chem. Soc., Chem. Comm., pp. 625-626.
Ojima, Iwao, et al., "Asymmetric Alkylation of Chiral (β-Lactam Ester Enolates. A New Approach to the Synthesis of α-Alkylated α-Amino Acids,," 1987, J. Am. Chem. Soc., Chem. Comm., pp. 6537-6540.
Ojima, Iwao, et al., "Asymmetric Alkylations of a Phenylalanylglycinate Equivalent. Novel Route to Dipeptides Bearing α-Alkyl-α-amoino Acid Residues," 1990, J. Am. Chem. Soc., vol. 112., pp. 770-774.
Serradeil-LeGal, et al., "Biochemical and Pharmacological Properties of SR 49059," J. Clin. Investigation, 1993, vol. 92, pp. 224-231.
R. Brouard et al., "Effect of SR49059, an orally active V1a vasopressin receptor antagonist, in the prevention of dysmenorrhoea", British Journal of Obstetrics and Gynecology, May 2000, vol. 107, pp. 614-619.

Primary Examiner — Mark Berch
(74) Attorney, Agent, or Firm — Barnes & Thornburg LLP

(57) ABSTRACT

Substituted 2-(azetidin-2-on-1-yl)alkoxyalkylalkanoic acids and 2-(azetidin-2-on-1-yl)arylalkylalkanoic acids, and analogs and derivatives thereof are described. Methods for using the described compounds, and pharmaceutical compositions thereof, to treat disease states responsive to antagonism of one or more vasopressin receptors are also described.

19 Claims, 1 Drawing Sheet

OTHER PUBLICATIONS

Jarrahpour, A.A., et al., "Asymmetric Synthesis and Antimicrobial Activity of Some New Mono and Bicyclic β-Lactams," Molecules, 2004, vol. 9, pp. 939-948.

Jarrahpour, A.A., et al., "Asymmetric Synthesis of a New Monocyclic β-Lactam as a potential biological active compound," Molecules, 2005, M439.

Ragner Liedman et al., "Intrauterine pressure, ischemia markers, and experienced pain during administration of a vasopressin V1a receptor antagonist in spontaneous and vasopressin-induced dysmenorrheal", Acta Obstetricia et Gynecologica. 85: 207-211, (2005).

PCT International Search Report for PCT/US2006/027703, dated Mar. 30, 2007.

PCT International Search Report for PCT/US2006/10192, dated Jul. 1, 2008.

European Search Report for EP 06739075.7, dated Sep. 22, 2011.

Brouard, R., "Effect of SR49059, an orally active V1a vasopressin receptor antagonist, in the prevention of dysmenorrhoea," British Journal of Obstetrics and Gynecology, May 2000, vol. 107, pp. 614-619.

* cited by examiner

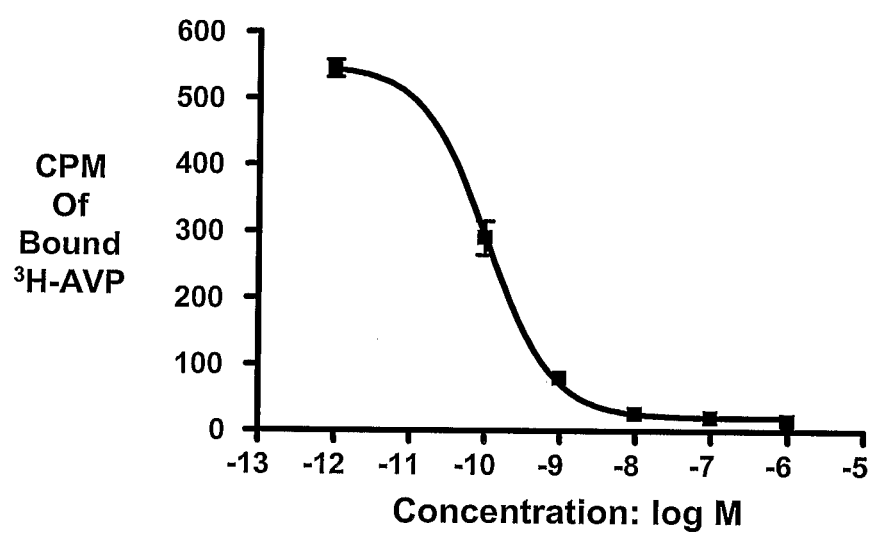

β-LACTAMYL PHENYLALANINE, CYSTEINE, AND SERINE VASOPRESSIN ANTAGONISTS

CROSS-REFERENCE TO RELATED APPLICATIONS

This application is a continuation application filed under 35 U.S.C. §120 of U.S. patent application Ser. No. 11/996,006, filed Feb. 18, 2008, which is a U.S. national application under 37 C.F.R. §371(b) of International Application Serial No. PCT/US2006/027703 filed Jul. 18, 2006, which claims the benefit under 35 U.S.C. §119(e) of U.S. provisional patent application Ser. No. 60/700,673, filed Jul. 19, 2005, the entirety of the disclosure of which are incorporated herein by reference.

TECHNICAL FIELD

The present invention relates to 2-(azetidin-2-on-1-yl)-substituted alkanoic acid analogs of amino acids. In particular, the invention relates to such alkanoic acid analogs of phenylalanine, cysteine, homocysteine, and homoserine, and analogs and derivatives thereof. The present invention also relates to methods for treating mammals in need of relief from disease states associated with and responsive to the antagonism of the vasopressin $V_{1a}$, $V_{1b}$, and $V_2$ receptors.

BACKGROUND

Arginine vasopressin (AVP) is a neurohypophyseal neuropeptide produced in the hypothalamus, and is involved in many biological processes in the circulatory system, the peripheral nervous system (PNS), and the central nervous system (CNS). In particular, AVP acts as a neurotransmitter in the brain. Several pharmacologically significant vasopressin receptor subtypes, including vasopressin $V_{1a}$, $V_{1b}$, and $V_2$, have been identified. Such vasopressin receptors are involved in several psychiatric, psychological, and behavioral disease states including depression, anxiety, affective disorders, and stress, as well as non-opioid mediation of tolerance for pain. Vasopressin receptors are also involved in a number of metabolic processes including water metabolism homeostasis, renal function, mediation of cardiovascular function, and regulation of temperature in mammals.

For example, AVP plays an important role in the onset of depression, one of the most common of the serious CNS disorders. Among the potential targets for treating depression is the hypothalamic-pituitary-adrenal-axis (HPA axis), which is perturbed in many depressed patients, as well as in stress-related affective disorders (see, Scott and Dinan, 1998; Serradiel-Le Gal et al., 2002, the disclosures of which are incorporated herein by reference). Normalization of HPA axis function appears to be a prerequisite for sustained remission of depressive symptoms when medication is used (see, Steckler, et al., 1999, the disclosures of which are incorporated herein by reference).

One of the signs of major depression is an elevated level of cortisol and ACTH associated with dysregulation of the HPA axis (see, Owens and Nemeroff, 1993; Plotsky et al. 1998, the disclosures of which are incorporated herein by reference). Corticotropin-releasing hormone (CRH) and arginine vasopressin (AVP) are the two main ACTH secretagogues, and recent preclinical and clinical studies have shown that AVP is important in mediating ACTH release during chronic psychological stress (see, Scott and Dinan, 1997, 1998, the disclosures of which are incorporated herein by reference). AVP is made in neurons localized to the paraventricular nucleus of the hypothalamus, and activation of these neurons causes the release of AVP into the portal circulation of the median eminence. However, the cortisol response to psychological stress appears to be regulated by AVP, but not by CRH in anxious healthy human volunteers (see, Boudarene et al., 1999, the disclosures of which are incorporated herein by reference). Chronic psychological stress accompanied by dysregulation of the HPA axis may contribute to the etiology of affective disorders. It has been found that many patients with major depression show elevated levels of AVP that decline as the mental illness improves (see, van Londen et al., 1997 & 2000, the disclosures of which are incorporated herein by reference).

AVP is also transported to the anterior pituitary where it can stimulate ACTH release by interacting with a $V_{1b}$ receptor on the cell membranes of corticotrophs. For example, rats selectively bred for high anxiety-related behavior show dysregulation in this HPA axis. Treatment with a $V_{1b}$ receptor antagonist can abolish CRH-stimulated ACTH secretion, demonstrating a shift in ACTH regulation from CRH to AVP (see, Keck et al., 1999, the disclosures of which are incorporated herein by reference). The presence of $V_{1b}$ receptors in several regions of the rat CNS and mouse CNS has also been demonstrated. It is therefore believed that $V_{1b}$ antagonists that penetrate the CNS may have greater therapeutic potential for stress-related affective disorders. Currently there are no vasopressin antagonists that are able to cross the blood brain barrier (Serradeil-Le Gal et al. 2002). There is also preclincial and clinical evidence that vasopressin, acting through a $V_{1b}$ receptor, contributes to a subtype of major depression associated with chronic stress and dysregulation of the HPA axis (see, Boudarene et al., 1999; Griebel et al., 2002; Scott and Dinan, 1997, 1998, the disclosures of which are incorporated herein by reference).

It has been reported that cardiovascular disease accounts for the largest cause of hospitalizations in individuals aged 65 years and older. It has been demonstrated that AVP contributes to the pathophysiology and progression of heart disease, including congestive heart, failure (see, Schrier & Abraham "Hormones and hemodynamics in heart failure," N. Engl. J. Med. 341:577-585 (1999); Thibonnier "Vasopressin receptor antagonists in heart failure," Curr. Op. Pharmacology 3:683-687 (2003); Lee et al., "Vasopressin: A new target for the treatment of heart failure," Am. Heart J. 146:9-18 (2003), the disclosures of which are incorporated herein by reference). In addition, the coordinated physiology of the renal/cardiovascular systems contributes to normal cardiac performance and homeostasis. Thus, AVP also plays an important role in water and electrolytic balance, regulation of blood volume, vascular smooth muscle tone, and cardiac contractility and metabolism. Each of these are major factors affecting the performance of the heart and its ability to meet the demands of the body. AVP affects all of these factors, in particular through activation of $V_{1a}$ and $V_2$ receptors. Vasopressin $V_{1a}$ receptors are localized to vascular smooth muscle and cardiomyocytes, promoting vasoconstriction and myocardial cell protein synthesis and growth, respectively. Vasopressin $V_2$ receptors are localized to the collecting ducts of nephrons in the kidney promoting free water reabsorption. Small changes in plasma osmolarity are sensed by receptors in the hypothalamus, which regulates the neurosecretory release of AVP from the pituitary gland. With osmotic stimulation, plasma AVP levels can rise from a basal level of 3-4 pg/ml to 9-10 pg/ml. These modest changes in AVP neurohormone level, in concert with the renin-angiotensin-aldosterone system, regulate the day-to-day water and electrolyte balance in healthy subjects.

However, it has been reported that the role of AVP in the cardiovascular physiology of healthy subjects is minimal, and for those persons, supraphysiological doses of neurohormone are needed to affect blood pressure, cardiac contractility, and coronary blood flow. In contrast, AVP plays a substantive role in patients with heart failure. For example, it has been observed that basal plasma levels of AVP are elevated in patients with heart failure as compared to healthy controls, particularly those that also present with hyponatremia (see, Goldsmith, "Congestive heart failure: potential role of arginine vasopressin antagonists in the therapy of heart failure," Congest, Heart Fail. 8:251-6 (2002); Schrier and Ecder, (2001), the disclosures of which are incorporated herein by reference). Further, the impaired water diuresis in congestive heart failure (CHF) patients leading to increased blood volume, hyponatremia, edema, and weight gain, is linked to AVP. With heart failure, elevations in plasma AVP lead to increased peripheral vascular resistance and pulmonary capillary wedge pressure while reducing cardiac output and stroke volume. Further, additional evidence suggests that AVP contributes to the hypertrophic myocardium characteristic of the failing heart (see, Nakamura et al., "Hypertrophic growth of cultured neonatal rat heart cells mediated by vasopressin $V_{1a}$ receptor," Eur J Pharmacol 391:39-48 (2000); Bird et al., "Significant reduction in cardiac fibrosis and hypertrophy in spontaneously hypertensive rats (SHR) treated with a $V_{1a}$ receptor antagonist," (abstract) Circulation 104:186 (2001), the disclosures of which are incorporated herein by reference), and cell/molecular studies have demonstrated that it also triggers a signaling cascade that promotes the myocardial fibrosis typically seen with progression of the disease.

Structural modification of vasopressin has provided a number of vasopressin agonists (see, Sawyer, *Pharmacol. Reviews,* 13:255 (1961)). In addition, several potent and selective vasopressin peptide antagonists have been disclosed (see, Lazslo et al., *Pharmacological Reviews,* 43:73-108 (1991); Mah and Hofbauer, *Drugs of the Future,* 12:1055-1070 (1987); Manning and Sawyer, *Trends in Neuroscience,* 7:8-9 (1984)). Further, novel structural classes of non-peptidyl vasopressin antagonists have been disclosed (see, Yamamura et al., *Science,* 275:572-574 (1991); Serradiel-Le Gal et al., *Journal of Clinical Investigation,* 92:224-231 (1993); Serradiel-Le Gal et al., *Biochemical Pharmacology,* 47(4):633-641 (1994)). Finally, the general structural class of substituted 2-(azetidin-2-on-1-yl)acetic acid esters and amides are known as synthetic intermediates for the preparation of β-lactam antibiotics (see, U.S. Pat. No. 4,751,299).

SUMMARY OF THE INVENTION

It has been discovered that certain compounds within the general class of substituted 2-(azetidin-2-on-1-yl)alkanoic acids and derivatives thereof are antagonists of vasopressin receptors, including vasopressin $V_{1a}$, $V_{1b}$, and $V_2$ receptors. Described herein are 2-(azetidin-2-on-1-yl)-substituted alkanoic acid analogs of phenylanlanine, cysteine, homocysteine, and homoserine, and analogs, homologs, and derivatives thereof. Also described herein are pharmaceutical compositions that include therapeutically effective amounts of the alkanoic acid compounds described herein for treating diseases and disorders that are responsive to antagonism of one or more vasopressin receptors, such as the $V_{1a}$, $V_{1b}$, or $V_2$ receptors. In addition, methods useful for treating diseases and disease states that are associated with vasopressin dysfunction, and that are responsive to antagonism of a vasopressin receptor, such as the $V_{1a}$, $V_{1b}$, or $V_2$ receptors, or a combination thereof, in a mammal are described. In addition, processes for preparing 2-(azetidin-2-on-1-yl)-substituted alkanoic acid analogs of phenylalanine, cysteine, homocysteine, and homoserine, and various analogs and derivatives thereof are described.

In one illustrative embodiment of the invention, compounds of formula (I) are described:

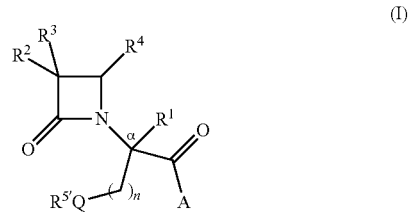

wherein:
Q is oxygen, sulfur, or oxidized sulfur, including —S(O)— and —$SO_2$—;
n is 1 or 2;
A is $R^5O$—, monosubstituted amino, disubstituted amino, or an optionally substituted nitrogen-containing heterocycle attached at a nitrogen;
$R^1$ is hydrogen or $C_1$-$C_6$ alkyl;
$R^2$ is hydrogen, alkyl, including $C_1$-$C_6$ alkyl, alkenyl, including $C_2$-$C_6$ alkenyl, such as vinyl, allyl, and the like, alkynyl, including $C_2$-$C_6$ alkynyl, such as ethynyl, propynyl, and the like, alkoxy, including $C_1$-$C_4$ alkoxy, alkylthio, including $C_1$-$C_4$ alkylthio, halo, haloalkyl, such as trifluoromethyl, trifluorochloroethyl, and the like, cyano, formyl, alkylcarbonyl, including $C_1$-$C_3$ alkylcarbonyl, alkoxycarbonyl, or a substituent selected from the group consisting of —$CO_2R^8$, —$CONR^8R^{8'}$, and —$NR^8(COR^9)$;
$R^3$ is an amino, amido, acylamido, or ureido group, which is optionally substituted; or $R^3$ is a nitrogen-containing heterocyclyl group attached at a nitrogen atom;
$R^4$ is alkyl, including $C_1$-$C_6$ alkyl, alkenyl, including $C_2$-$C_6$ alkenyl, alkynyl, including $C_2$-$C_6$ alkynyl, cycloalkyl, including $C_3$-$C_8$ cycloalkyl, cycloalkenyl, including $C_3$-$C_9$ cycloalkenyl, such as limonenyl, pinenyl, and the like, alkylcarbonyl, including $C_1$-$C_3$ alkylcarbonyl, optionally substituted aryl, optionally substituted arylalkyl, including aryl($C_1$-$C_4$ alkyl), optionally substituted arylhaloalkyl, optionally substituted arylalkoxyalkyl, optionally substituted arylalkenyl, including aryl($C_2$-$C_4$ alkenyl), optionally substituted arylhaloalkenyl, or optionally substituted arylalkynyl, including aryl($C_2$-$C_4$ alkynyl);
$R^5$ is selected from hydrogen, alkyl, including $C_1$-$C_6$ alkyl, cycloalkyl, including $C_3$-$C_8$ cycloalkyl, alkoxyalkyl, including ($C_1$-$C_4$ alkoxy)-($C_1$-$C_4$ alkyl), optionally substituted arylalkyl, including aryl($C_1$-$C_4$ alkyl), heterocyclyl, heterocyclyl($C_1$-$C_4$ alkyl), and $R^6R^7N$—($C_2$-$C_4$ alkyl), where heterocyclyl is in each occurrence independently selected from tetrahydrofuryl, morpholinyl, pyrrolidinyl, piperidinyl, piperazinyl, homopiperazinyl, or quinuclidinyl; where said morpholinyl, pyrrolidinyl, piperidinyl, piperazinyl, homopiperazinyl, or quinuclidinyl is optionally N-substituted with $C_1$-$C_4$ alkyl or optionally substituted aryl($C_1$-$C_4$ alkyl);
$R^{5'}$ is selected from the group consisting of —$SR^{15}$, —$S(O)R^{15}$, —$SO_2R^{15}$, $C_1$-$C_6$ alkyl, $C_3$-$C_8$ cycloalkyl, ($C_1$-$C_4$ alkoxy)-($C_1$-$C_4$ alkyl), optionally-substituted arylalkyl, including aryl($C_1$-$C_4$ alkyl), heterocyclyl, heterocyclyl($C_1$-$C_4$ alkyl), and $R^{6'}R^{7'}N$—($C_2$-$C_4$ alkyl); where heterocyclyl is in each occurrence independently selected from tetrahydrofuryl, morpholinyl, pyrrolidinyl, piperidinyl, piperazinyl, homopiperazinyl, or quinuclidinyl; where said morpholinyl, pyrrolidinyl, piperidinyl, piperazinyl, homopiperazinyl, or quinuclidinyl is optionally N-substituted with $C_1$-$C_4$ alkyl or optionally substituted aryl($C_1$-$C_4$ alkyl);

$R^6$ is hydrogen or alkyl, including $C_1$-$C_6$ alkyl, and $R^7$ is alkyl, including $C_1$-$C_6$ alkyl, cycloalkyl, including $C_3$-$C_8$ cycloalkyl, optionally substituted aryl, or optionally substituted arylalkyl, including aryl($C_1$-$C_4$ alkyl); or $R^6$ and $R^7$ are taken together with the attached nitrogen atom to form an heterocycle, such as pyrrolidinyl, piperidinyl, morpholinyl, piperazinyl, and homopiperazinyl; where said piperazinyl or homopiperazinyl is optionally N-substituted with $R^{13}$;

$R^{6'}$ is hydrogen or alkyl, including $C_1$-$C_6$ alkyl, and $R^{7'}$ is alkyl, including $C_1$-$C_6$ alkyl, cycloalkyl, including $C_3$-$C_8$ cycloalkyl, optionally substituted aryl, or optionally substituted arylalkyl, including aryl($C_1$-$C_4$ alkyl); or $R^{6'}$ and $R^{7'}$ are taken together with the attached nitrogen atom to form an heterocycle, such as pyrrolidinyl, piperidinyl, morpholinyl, piperazinyl, and homopiperazinyl; where said piperazinyl or homopiperazinyl is optionally N-substituted with $R^{13'}$;

$R^8$ and $R^{8'}$ are each independently selected in each instance from hydrogen, alkyl, including $C_1$-$C_6$ alkyl, cycloalkyl, including $C_3$-$C_8$ cycloalkyl, optionally substituted aryl, or optionally substituted arylalkyl, including aryl($C_1$-$C_4$ alkyl); or $R^8$ and $R^{8'}$ are taken together with the attached nitrogen atom to form an heterocycle, such as optionally substituted pyrrolidinyl, piperidinyl, morpholinyl, piperazinyl, and homopiperazinyl;

$R^9$ is selected from hydrogen, alkyl, including $C_1$-$C_6$ alkyl, cycloalkyl, including $C_3$-$C_8$ cycloalkyl, alkoxyalkyl, including ($C_1$-$C_4$ alkoxy)-($C_1$-$C_4$ optionally substituted aryl, optionally substituted arylalkyl, including aryl($C_1$-$C_4$ alkyl), optionally substituted heteroaryl, optionally substituted heteroarylalkyl, including heteroaryl($C_1$-$C_4$ alkyl), and $R^8R^{8'}N$—($C_1$-$C_4$ alkyl);

$R^{13}$ and $R^{13'}$ are each independently selected from hydrogen, alkyl, including $C_1$-$C_6$ alkyl, cycloalkyl, including $C_3$-$C_8$ cycloalkyl, alkoxycarbonyl, including $C_1$-$C_4$ alkoxycarbonyl, optionally substituted aryloxycarbonyl, optionally substituted arylalkyl, including aryl($C_1$-$C_4$ alkyl), and optionally substituted aryloyl;

$R^{15}$ is selected from the group consisting of $C_1$-$C_6$ alkyl, $C_3$-$C_8$ cycloalkyl, ($C_1$-$C_4$ alkoxy)-($C_1$-$C_4$ alkyl), optionally-substituted aryl($C_1$-$C_4$ alkyl), Y', Y'—($C_1$-$C_4$ alkyl), and $R^{6'}R^{7'}N$—($C_2$-$C_4$ alkyl); and hydrates, solvates, and pharmaceutically acceptable salts thereof;

provided that when Q is oxygen, n is 2 and $R^{5'}$ is not —$SR^{15}$, —$S(O)R^{15}$, or —$SO_2R^{15}$.

In another illustrative embodiment of the invention, compounds of formula (II) are described:

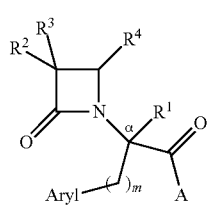

(II)

wherein:
Aryl is an optionally substituted monocyclic or polycyclic aromatic group;
m is 1, 2, 3, or 4; and
A, $R^1$, $R^2$, $R^3$, and $R^4$ are as defined in formula (I); and
hydrates, solvates, and pharmaceutically acceptable salts thereof.

In another illustrative embodiment of the invention, compounds of formula (III) are described:

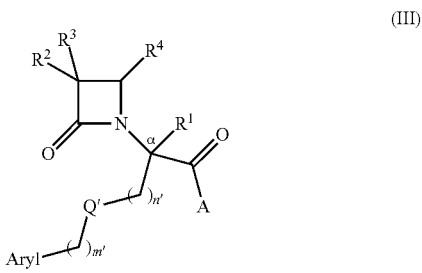

(III)

wherein:
Aryl is an optionally substituted monocyclic or polycyclic aromatic group;
Q' is oxygen, sulfur, or —$CH_2$—;
n' is 0, 1, or 2;
m' is 0, 1, or 2; and
A, $R^1$, $R^2$, $R^3$, and $R^4$ are as defined in formula (I); and
hydrates, solvates, and pharmaceutically acceptable salts thereof,
provided that when Q' is oxygen, n' is 2; and when Q' is sulfur, n' is 1 or 2.

In one aspect, compounds of formula (I) are described, wherein Q is oxygen, and n is 2. In another aspect, compounds of formula (I) are described, wherein Q is sulfur, and n is 1 or 2. In another aspect, compounds of formula (I) are described, wherein Q is sulfur, n is 1, and $R^{5'}$ is alkyl or optionally substituted arylalkyl. In another aspect, compounds of formula (I) are described, wherein Q is sulfur, n is 2, and $R^{5'}$ is alkyl or optionally substituted arylalkyl.

In one aspect of the compounds of formulae (II) and (III), Aryl is optionally substituted phenyl, including phenyl, alkylphenyl, hydroxyphenyl, alkoxyphenyl, halophenyl, cyanophenyl, and the like; optionally substituted pyridinyl, including 2-, 3-, and 4-pyridinyl, alkyl 2-, 3-, and 4-pyridinyl, halo 2-, 3-, and 4-pyridinyl, and the like; and optionally substituted naphthyl, including 2-, and 3-naphthyl, alkyl-naphthyl, hydroxynaphthyl, alkoxynaphthyl, halonaphthyl, and the like.

It is to be understood that various aspects of the formulae described herein may be selected in many combinations. Illustratively, for any of the compounds of formulae (I), (II), or (III), compounds are selected where $R^2$ is hydrogen, $R^4$ is an arylalkenyl, and A is either a monosubstituted amino, a disubstituted amino, or an optionally substituted nitrogen-containing heterocycle. In variations, compounds are selected where $R^2$ is hydrogen or methyl, $R^4$ is an arylalkyl, and A is either a monosubstituted amino, a disubstituted amino, or an optionally substituted nitrogen-containing heterocycle. In another illustrative combination for compounds of formulae (I) and $R^2$ is hydrogen, $R^4$ is an arylalkyl, and Q or Q' is sulfur. In variations, A is either a monosubstituted amino, a disubstituted amino, or an optionally substituted nitrogen-containing heterocycle, and n or n' is 1. In other variations, $R^1$ is hydrogen, and in still other variations, $R^4$ is more specifically optionally substituted phenylethenyl. Is to be further understood that such variations may be further combined to define subsets of compounds selected from the invention described herein.

In another embodiment, pharmaceutical compositions are described herein, where the pharmaceutical compositions include one or more of the compounds described herein, including but not limited to the compounds of formulae (I), (II), or (III), and/or 2-(azetidin-2-on-1-yl)-substituted analogs of phenylalanine, cysteine, homocysteine, and homoserine, and derivatives and analogs thereof described herein, and combinations thereof. The 2-(azetidin-2-on-1-yl)-substituted analogs of phenylalanine, cysteine, homocysteine, and homoserine and derivatives and analogs thereof include compounds of formulae (I), (II), or (III). The pharmaceutical compositions described herein also include one or more pharmaceutically acceptable carriers, diluents, and/or excipients. In one illustrative aspect, pharmaceutical compositions are described that exhibit oral activity and/or oral bioavailability. In another illustrative aspect, pharmaceutical compositions are described that allow the 2-(azetidin-2-on-1-yl)-substituted analogs of phenylalanine, cysteine, homocysteine, and homoserine, and derivatives and analogs thereof to cross the blood brain barrier.

In another embodiment, methods for treating disease states responsive to the antagonism of a vasopressin $V_{1a}$, $V_{1b}$, and/or $V_2$ receptors, in a mammal in need of such treatment are described. The methods comprise the step of administering to the mammal a pharmaceutically effective amount of one or more of the compounds described herein, including but not limited to the compounds of formulae (I), (II), or (III), and/or 2-(azetidin-2-on-1-yl)-substituted analogs of phenylalanine, cysteine, homocysteine, and homoserine, and derivatives and analogs thereof described herein, and combinations thereof. In another embodiment, the methods comprise the step of administering to the mammal a composition containing a pharmaceutically effective amount of one or more 2-(azetidin-2-on-1-yl)-substituted analogs of phenylalanine, cysteine, homocysteine, and homoserine, and derivatives and analogs thereof described herein, and a pharmaceutically acceptable carrier, diluent, or excipient.

Illustrative disease states that are responsive to the antagonism of one or more of the vasopressin $V_{1a}$, $V_{1b}$, and/or $V_2$ receptors, and treatable by the methods described herein, include various stress-related mental illnesses, depression, anxiety, affective disorders, obsessive-compulsive disease, impulsivity, aggressive disorders, and the like; diseases affecting water homeostasis, renal function, inhibition of phosphatidyl inositol turnover, temperature regulation, and the like; diseases associated with nausea, emesis, and pain; and various cardiovascular diseases, including congestive heart failure, disorders or conditions associated with platelet aggregation, and the like. In addition, methods for treating other disease states and conditions treatable by, for example, oxytocin receptor antagonism, tachykinin receptor antagonism, neurokinin 1 receptor antagonism, neurokinin 2 receptor antagonism, and the like are described herein, where the method includes the step of administering to a patient in need of relief from such a disease state or condition an effective amount of one or more 2-(azetidin-2-on-1-yl)-substituted analogs of phenylalanine, cysteine, homocysteine, and homoserine, and derivatives and analogs thereof described herein, including the compounds of formulae (I), (II), or (III); or the method includes the step of administering to a patient in need of relief from such a disease state or condition a composition described herein, where the composition includes an effective amount of one or more 2-(azetidin-2-on-1-yl)-substituted analogs of phenylalanine, cysteine, homocysteine, and homoserine, and derivatives and analogs thereof described herein, including the compounds of formulae (I), (II), or (III), and a pharmaceutically acceptable carrier, diluent, and/or excipient.

BRIEF DESCRIPTION OF THE DRAWING

FIG. 1 shows the human $V_{1b}$ binding affinity (Ki=0.07 nM) of Example 9B through a competitive binding assay conducted in CHO cells transfected with human $V_{1a}$ receptor.

DETAILED DESCRIPTION

The general chemical terms used in the formulae described herein have their usual ordinary meanings. For example, the term "alkyl" refers to a straight-chain or optionally branched, saturated hydrocarbon, including but not limited to methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like.

The term "cycloalkyl" refers to a straight-chain or optionally branched, saturated hydrocarbon, at least a portion of which forms a ring, including but not limited to cyclopropyl, cyclobutyl, cyclopentyl, methylcyclopentyl, cyclohexyl, cycloheptyl, cyclooctyl, and the like.

The term "alkenyl" refers to a straight-chain or optionally branched, hydrocarbon that includes at least one double bond, including but not limited to vinyl or ethenyl, allyl or propenyl, isopropenyl, 2-butenyl, 2-methyl-2-propenyl, butadienyl, and the like.

The term "alkynyl" refers to a straight-chain or optionally branched, hydrocarbon that includes at least one triple bond, including but not limited to ethynyl, propynyl, 1-butynyl, hex-4-en-2-ynyl, and the like.

The term "aryl" refers to an aromatic ring or heteroaromatic ring and includes such groups as furyl, pyrrolyl, thienyl, pyridinyl, thiazolyl, oxazolyl, isoxazolyl, isothiazolyl, imidazolyl, pyrazolyl, phenyl, pyridazinyl, pyrimidinyl, pyrazinyl, thiadiazolyl, oxadiazolyl, naphthyl, indanyl, fluorenyl, quinolinyl, isoquinolinyl, benzodioxanyl, benzofuranyl, benzothienyl, and the like.

The term "optionally substituted" refers to the replacement of one or more, illustratively from one to about three, hydrogen atoms with one or more substitutents. Substituents include but are not limited to such groups as $C_1$-$C_4$ alkyl, $C_1$-$C_4$ alkoxy, $C_1$-$C_4$ alkylthio, hydroxy, nitro, halo, carboxy, cyano, $C_1$-$C_4$ haloalkyl, $C_1$-$C_4$ haloalkoxy, amino, carbamoyl, carboxamide, amino, alkylamino, dialkylamino, alkylalkylamino, $C_1$-$C_4$ alkylsulfonylamino, and the like.

The term "heterocycle" refers to a non-aromatic cyclic structure possessing one or more heteroatoms, such as nitrogen, oxygen, sulfur, and the like, and includes such groups as tetrahydrofuryl, morpholinyl, pyrrolidinyl, piperidinyl, piperazinyl, homopiperazinyl, quinuclidinyl, and the like.

The term "alkoxy" refers to an alkyl or cycloalkyl substituent attached through an oxygen, and includes such groups as methoxy, ethoxy, propoxy, isopropoxy, butoxy, tert-butoxy and the like.

The term "acyl" includes terms such as "alkanoyl," and "aroyl" and refers to alkyl, alkenyl, alkyl, aryl, and the like attached through a carbonyl group. Illustratively, acyl is formyl, acetyl, propanoyl, butanoyl, pentanoyl, cyclohexanoyl, optionally substituted benzoyl, and the like.

The term "halo" refers to fluoro, chloro, bromo, and iodo.

The term "alkanoyloxy" includes such groups as formyloxy, acetoxy, n-propionoxy, n-butyroxy, pivaloyloxy, and like lower alkanoyloxy groups.

The terms "optionally substituted $C_1$-$C_4$ alkyl," "optionally substituted $C_3$-$C_8$ cycloalkyl," and "optionally substituted $C_2$-$C_4$ alkenyl" refer to alkyl, cycloalkyl, or alkenyl, respectively, optionally substituted with a substituent as described herein, including but not limited to hydroxy, protected hydroxy, alkyl, protected carboxyl, carbamoyl, benzylthio, alkylthio, and the like.

The term "($C_1$-$C_4$ alkyl)" as used in for example "aryl($C_1$-$C_4$ alkyl)", "($C_1$-$C_4$ alkoxy)-($C_1$-$C_4$ alkyl)", and the like, refers to a saturated linear or branched divalent alkyl chain of from one to four carbons having for example aryl, $C_1$-$C_4$ alkoxy, and the like, as a substituent and includes such groups as for example benzyl, phenethyl, phenpropyl, α-methylbenzyl, methoxymethyl, ethoxyethyl, and the like.

The term "optionally substituted phenyl" is taken to mean a phenyl radical optionally substituted with one or more substituents each independently selected, such as $C_1$-$C_4$ alkyl, $C_1$-$C_4$ alkoxy, hydroxy, halo, nitro, trifluoromethyl, sulfonamido, cyano, carbamoyl, amino, mono($C_1$-$C_4$ alkyl)amino, di($C_1$-$C_4$ alkyl)amino, alkylsulfonylamino, and indol-2-yl.

The term "protected amino" refers to amine protected by a protecting group that may be used to protect the nitrogen, such as the nitrogen in the β-lactam ring, during preparation or subsequent reactions. Examples of such groups are benzyl, 4-methoxybenzyl, 4-methoxyphenyl, trialkylsilyl, for example trimethylsilyl, and the like.

The term "protected carboxy" refers to the carboxy group protected or blocked by a conventional protecting group commonly used for the temporary blocking of the acidic carboxy. Examples of such groups include lower alkyl, for example tert-butyl, halo-substituted lower alkyl, for example 2-iodoethyl and 2,2,2-trichloroethyl, benzyl and substituted benzyl, for example 4-methoxybenzyl and 4-nitrobenzyl, diphenylmethyl, alkenyl, for example allyl, trialkylsilyl, for example trimethylsilyl and tert-butyldiethylsilyl and like carboxy-protecting groups.

It is to be understood that in the embodiments described herein, an illustrative variation of alkyl is $C_1$-$C_6$ alkyl, such as methyl, ethyl, propyl, prop-2-yl, and the like; an illustrative variation of alkenyl is $C_2$-$C_6$ alkenyl, such as vinyl, allyl, and the like; an illustrative variation of alkynyl is $C_2$-$C_6$ alkynyl, such as ethynyl, propynyl, and the like; an illustrative variation of alkoxy is $C_1$-$C_4$ alkoxy, such as methoxy, pent-3-oxy, and the like; an illustrative variation of alkylthio is $C_1$-$C_4$ alkylthio, such as ethylthio, 3-methylbuty-2-ylthio, and the like; an illustrative variation of alkylcarbonyl is $C_1$-$C_3$ alkylcarbonyl, such as acetyl, propanoyl, and the like; an illustrative variation of cycloalkyl is $C_3$-$C_8$ cycloalkyl; an illustrative variation of cycloalkenyl is $C_3$-$C_9$ cycloalkenyl, such as limonenyl, pinenyl, and the like; an illustrative variation of optionally substituted arylalkyl is optionally substituted aryl($C_1$-$C_4$ alkyl); an illustrative variation of optionally substituted arylalkenyl is optionally substituted aryl($C_2$-$C_4$ alkenyl); an illustrative variation of optionally substituted arylalkynyl is optionally substituted aryl($C_2$-$C_4$ alkynyl); an illustrative variation of alkoxyalkyl is ($C_1$-$C_4$ alkoxy)-($C_1$-$C_4$ alkyl); an illustrative variation of optionally substituted heteroarylalkyl is optionally substituted heteroaryl($C_1$-$C_4$ alkyl); and an illustrative variation of alkoxycarbonyl is $C_1$-$C_4$ alkoxycarbonyl.

The term "antagonist", as used herein, refers to a full or partial antagonist. While a partial antagonist of any intrinsic activity may be useful, the partial antagonists illustratively show at least about 50% antagonist effect, or at least about 80% antagonist effect. The term also includes compounds that are full antagonists of the vasopressin $V_{1b}$ receptor. It is appreciated that illustrative methods described herein require therapeutically effective amounts of vasopressin $V_{1b}$ receptor antagonists; therefore, compounds exhibiting partial antagonism at the vasopressin $V_{1b}$ receptor may be adminstered in higher doses to exhibit sufficient antagonist activity to inhibit the effects of vasopressin or a vasopressin agonist.

In one aspect of the compounds of formula (I), A is monosubstituted amino, disubstituted amino, or an optionally substituted nitrogen-containing heterocycle attached at a nitrogen.

In another aspect, compounds of formula (I) are described, wherein Q is oxygen, and n is 2. In another aspect, compounds of formula (I) are described, wherein Q is sulfur, and n is 1 or 2. In another aspect, compounds of formula (I) are described, wherein Q is sulfur, n is 2, and $R^{5'}$ is alkyl or optionally substituted arylalkyl. In another aspect, compounds of formula (I) are described, wherein Q is sulfur, n is 2, and $R^{5'}$ is alkylthio or optionally substituted arylalkylthio.

In one aspect of the compounds of formulae (II) and (III), Aryl is optionally substituted phenyl, including phenyl, alkylphenyl, hydroxyphenyl, alkoxyphenyl, halophenyl, cyanophenyl, and the like; optionally substituted pyridinyl, including 2-, 3-, and 4-pyridinyl, alkyl 2-, 3-, and 4-pyridinyl, halo 2-, 3-, and 4-pyridinyl, and the like; and optionally substituted naphthyl, including 2-, and 3-naphthyl, alkylnaphthyl, hydroxynaphthyl, alkoxynaphthyl, halonaphthyl, and the like.

In another aspect, compounds of formula (II) are described, wherein Aryl is optionally substituted phenyl, including phenyl, alkylphenyl, hydroxyphenyl, alkoxyphenyl, halophenyl, cyanophenyl, and the like; optionally substituted pyridinyl, including 2-, 3-, and 4-pyridinyl, alkyl 2-, 3-, and 4-pyridinyl, halo 2-, 3-, and 4-pyridinyl, and the like; and optionally substituted naphthyl, including 2-, and 3-naphthyl, alkylnaphthyl, hydroxynaphthyl, alkoxynaphthyl, halonaphthyl, and the like.

In another aspect, compounds of formula (II) are described, wherein $R^{5'}$ is optionally substituted alkyl, including optionally substituted $C_1$-$C_6$ alkyl, $C_1$-$C_4$ alkyl, and $C_1$-$C_2$ alkyl. In another aspect, compounds of formula (II) are described, wherein $R^{5'}$ is optionally substituted aryl($C_1$-$C_4$ alkyl), including phenyl($C_1$-$C_4$ alkyl), or optionally substituted aryl($C_1$-$C_2$ alkyl).

In another aspect, compounds of formula (III) are described wherein n' and m' are each the integer 1.

In another aspect, compounds of formulae (II) and (III) are described wherein Aryl is optionally substituted phenyl. In another aspect, compounds of formulae (II) and (III) are described wherein m and m' are each the integer 1.

In another aspect, compounds of formulae (I), (II), and (III) are described, wherein A is a monosubstituted amino. In another aspect, compounds of formula (I) are described, wherein A is a disubstituted amino. In another aspect, compounds of formula (I) are described, wherein A is an optionally substituted nitrogen-containing heterocycle attached at a nitrogen.

In another aspect, compounds of formulae (I), (II), and (III) are described, wherein A is an amino group of the formula $R^{14}XN$—; where $R^{14}$ is selected from the group consisting of hydrogen, hydroxy, alkyl, including $C_1$-$C_6$ alkyl, alkoxycarbonyl, including $C_1$-$C_4$ alkoxycarbonyl, and benzyl; and where X is selected from the group consisting of alkyl, including $C_1$-$C_6$ alkyl, cycloalkyl, including $C_3$-$C_8$ cycloalkyl, alkoxyalkyl, including ($C_1$-$C_4$ alkoxy)-($C_1$-$C_4$ alkyl), optionally substituted aryl, optionally substituted arylalkyl, including optionally substituted aryl($C_1$-$C_4$ alkyl), and a group Y, Y—($C_1$-$C_4$ alkyl), $R^6R^7N$—, and $R^6R^7N$—($C_2$-$C_4$ alkyl), where Y is an heterocycle. In one variation of the compounds of formulae (I), (II), and (III), $R^{14}$ is hydrogen.

In another aspect, compounds of formulae (I), (II), and (III) are described, wherein A is a heterocycle having the formula $R^{14}XN$—, where $R^{14}$ and X, are taken together with the attached nitrogen atom to form the heterocycle, such as an heterocycle selected from the group consisting of pyrrolidinyl, piperidinyl, piperazinyl, and homopiperazinyl; where the heterocycle is optionally substituted with $R^{10}$, $R^{12}$, $R^6R^7N$—, or $R^6R^7N$—($C_1$-$C_4$ alkyl) as defined above.

In one variation, compounds of formulae (I), (II), and (III) are described wherein $R^{14}$ and X are taken together with the attached nitrogen atom to form piperidinyl optionally substituted at the 4-position with hydroxy, alkyl, including $C_1$-$C_6$ alkyl, cycloalkyl, including $C_3$-$C_8$ cycloalkyl, alkoxy, including $C_1$-$C_4$ alkoxy, alkoxycarbonyl, including ($C_1$-$C_4$ alkoxy)carbonyl, hydroxyalkyloxyalkyl, including (hydroxy($C_2$-$C_4$ alkyloxy))-($C_2$-$C_4$ alkyl), $R^6R^7N$—, $R^6R^7N$-alkyl, including $R^6R^7N$—($C_1$-$C_4$ alkyl), diphenylmethyl, optionally substituted aryl, optionally substituted aryl($C_1$-$C_4$ alkyl), or piperidin-1-yl($C_1$-$C_4$ alkyl).

In another variation, compounds of formulae (I), (II), and (III) are described wherein $R^{14}$ and X are taken together with the attached nitrogen atom to form piperazinyl optionally substituted at the 4-position with alkyl, including $C_1$-$C_6$ alkyl, cycloalkyl, including $C_3$-$C_8$ cycloalkyl, optionally substituted aryl, optionally substituted arylalkyl, including optionally substituted aryl($C_1$-$C_4$ alkyl), α-methylbenzyl, and the like, N-alkyl acetamid-2-yl, including N—($C_1$-$C_5$ alkyl)acetamid-2-yl, N-(cycloalkyl)acetamid-2-yl, including N—($C_3$-$C_8$ cycloalkyl)acetamid-2-yl, $R^6R^7N$—, $R^{6'}R^{7'}N$—, or alkoxycarbonyl, including ($C_1$-$C_4$ alkoxy)carbonyl.

In another variation, compounds of formulae (I), (II), and (III) are described wherein A is a disubstituted amino having the formula $R^{14}XN$—, where $R^{14}$ and X are taken together with the attached nitrogen atom to form piperidinyl optionally substituted in the 4-position with alkyl, including $C_1$-$C_4$ alkyl, or heterocyclyl($C_1$-$C_4$ alkyl).

In another variation, compounds of formulae (I), (II), and (III) are described, wherein A is a disubstituted amino having the formula $R^{14}XN$— where $R^{14}$ and X are taken together with the attached nitrogen atom to form piperidinyl optionally substituted in the 4-position with piperadinyl($C_1$-$C_4$ piperazinyl($C_1$-$C_4$ alkyl), or pyrrolidinyl($C_1$-$C_4$ alkyl).

In another aspect, compounds of formulae (I), (II), and (III) are described, wherein A is a monosubstituted amino. In another aspect, compounds of formulae (I), (II), and (III) are described, wherein A is a disubstituted amino. In another aspect, compounds of formulae (I), (II), and (III)) are described, wherein A is an optionally substituted nitrogen-containing heterocycle attached at a nitrogen.

In another aspect, compounds of formulae (I), (II), and (III) are described, wherein A is a monosubstituted amino having the formula XNH—, where X is selected from the group consisting of alkyl, including $C_1$-$C_6$ alkyl, cycloalkyl, including $C_3$-$C_8$ cycloalkyl, alkoxyalkyl, including ($C_1$-$C_4$ alkoxy)-($C_1$-$C_4$ alkyl), optionally substituted aryl, optionally substituted arylalkyl, including optionally substituted aryl($C_1$-$C_4$ alkyl), and a group Y, Y—($C_1$-$C_4$ alkyl), $R^6R^7N$—, and $R^6R^7N$—($C_2$-$C_4$ alkyl), where Y is an heterocycle.

In another aspect, compounds of formulae (I), (II), and (III) are described, wherein A is a disubstituted amino having the formula $R^{14}XN$—; where $R^{14}$ is selected from the group consisting of hydroxy, alkyl, including $C_1$-$C_6$ alkyl, alkoxycarbonyl, including $C_1$-$C_4$ alkoxycarbonyl, and benzyl; and where X is selected from the group consisting of alkyl, including $C_1$-$C_6$ alkyl, cycloalkyl, including $C_3$-$C_8$ cycloalkyl, alkoxyalkyl, including ($C_1$-$C_4$ alkoxy)-($C_1$-$C_4$ alkyl), optionally substituted aryl, optionally substituted arylalkyl, including optionally substituted aryl($C_1$-$C_4$ alkyl), and a group Y, Y—($C_1$-$C_4$ alkyl), $R^6R^7N$—, and $R^6R^7N$—($C_2$-$C_4$ alkyl), where Y is an heterocycle.

In another aspect, compounds of formulae (I), (II), and (III) are described, wherein A is an optionally substituted heterocycle having the formula $R^{14}XN$—, where $R^{14}$ and X are taken together with the attached nitrogen atom to form the heterocycle, such as an heterocycle selected from the group consisting of pyrrolidinyl, piperidinyl, piperazinyl, and homopiperazinyl; where the heterocycle is optionally substituted with $R^{10}$, $R^{12}$, $R^6R^7N$—, or $R^6R^7N$—($C_1$-$C_4$ alkyl) as defined above.

In another aspect, compounds of formulae (I), (II), and (III) are described wherein $R^{14}$ and X, are taken together with the attached nitrogen atom to form piperidinyl optionally substituted at the 4-position with hydroxy, alkyl, including $C_1$-$C_6$ alkyl, cycloalkyl, including $C_3$-$C_8$ cycloalkyl, alkoxy, including $C_1$-$C_4$ alkoxy, alkoxycarbonyl, including ($C_1$-$C_4$ alkoxy)carbonyl, hydroxyalkyloxyalkyl, including (hydroxy($C_2$-$C_4$ alkyloxy))-($C_2$-$C_4$ alkyl), $R^6R^7N$—, $R^6R^7N$-alkyl, including $R^6R^7N$— ($C_1$-$C_4$ alkyl), diphenylmethyl, optionally substituted aryl, optionally substituted aryl($C_1$-$C_4$ alkyl), or piperidin-1-yl($C_1$-$C_4$ alkyl).

In another aspect, compounds of formulae (I), (II), and (III) are described wherein $R^{14}$ and X are taken together with the attached nitrogen atom to form piperazinyl optionally substituted at the 4-position with alkyl, including $C_1$-$C_6$ alkyl, cycloalkyl, including $C_3$-$C_8$ cycloalkyl, optionally substituted aryl, optionally substituted arylalkyl, including optionally substituted aryl($C_1$-$C_4$ alkyl), α-methylbenzyl, and the like, N-alkyl acetamid-2-yl, including N—($C_1$-$C_5$ alkyl)acetamid-2-yl, N-(cycloalkyl)acetamid-2-yl, including N—($C_3$-$C_8$ cycloalkyl)acetamid-2-yl, $R^6R^7N$—, $R^{6'}R^{7'}N$—, or alkoxycarbonyl, including ($C_1$-$C_4$ alkoxy)carbonyl.

Illustrative compounds of formulae (I), (II), and (III) are described wherein A is a disubstituted amino having the formula $R^{14}XN$—, where $R^{14}$ and X are taken together with the attached nitrogen atom to form piperadinyl optionally substituted in the 4-position with alkyl, including $C_1$-$C_4$ alkyl, or heterocyclyl($C_1$-$C_4$ alkyl).

Illustrative compounds of formulae (I), (II), and (III) are described,
wherein A is a disubstituted amino having the formula $R^{14}XN$— where $R^{14}$ and X are taken together with the attached nitrogen atom to form piperadinyl optionally substituted in the 4-position with piperadinyl($C_1$-$C_4$ alkyl), piperazinyl($C_1$-$C_4$ alkyl), or pyrrolidinyl($C_1$-$C_4$ alkyl).

Illustrative compounds of formulae (I), (II), and (III) are described, wherein $R^{14}$ and X are taken together with the attached nitrogen atom to form homopiperazinyl optionally substituted in the 4-position with alkyl, including $C_1$-$C_4$ alkyl, aryl, or aryl($C_1$-$C_4$ alkyl).

Illustrative compounds of formulae (I), (II), and (III) are described, wherein A is a disubstituted amino having the formula $R^{14}XN$—, where $R^{14}$ and X are taken together with the attached nitrogen atom to form an heterocycle selected from the group consisting of pyrrolidinonyl, piperidinonyl, 2-(pyrrolidin-1-ylmethyl)pyrrolidin-1-yl, and 1,2,3,4-tetrahydroisoquinolin-2-yl.

In another aspect of the compounds of formulae (I), (II), or (III), $R^3$ is a structure selected from the group consisting of

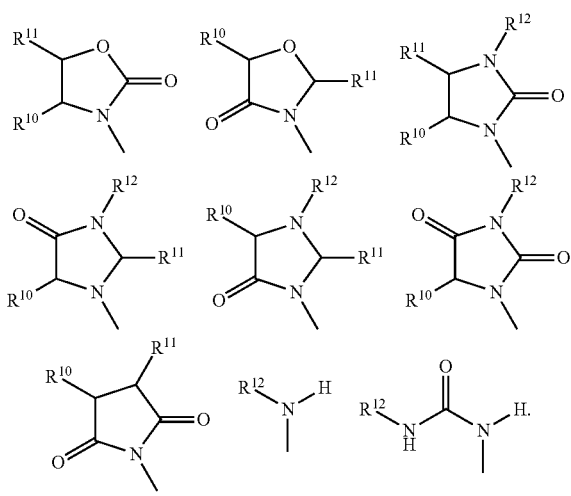

wherein $R^{10}$ and $R^{11}$ are each independently selected from hydrogen, optionally substituted alkyl, including $C_1$-$C_6$ alkyl, optionally substituted cycloalkyl, including $C_3$-$C_8$ cycloalkyl, alkoxyalkyl, including $C_1$-$C_4$ alkoxycarbonyl, alkylcarbonyloxy, including $C_1$-$C_5$ alkylcarbonyloxy, optionally substituted aryl, optionally substituted arylalkyl, including aryl($C_1$-$C_4$ alkyl), optionally substituted arylalkyloxy, including aryl($C_1$-$C_4$ alkyloxy), optionally substituted arylalkylcarbonyloxy, including aryl($C_1$-$C_4$ alkylcarbonyloxy), diphenylmethoxy, and triphenylmethoxy; and $R^{12}$ is selected from hydrogen, alkyl, including $C_1$-$C_6$ alkyl, cycloalkyl, including $C_3$-$C_8$ cycloalkyl, alkoxycarbonyl, including $C_1$-$C_4$ alkoxycarbonyl, optionally substituted aryloxycarbonyl, optionally substituted arylalkyl, including aryl($C_1$-$C_4$ alkyl), and optionally substituted aryloyl.

In another aspect, compounds of formulae (I), (II), or (III) are described, wherein $R^3$ is a structure selected from the group consisting of

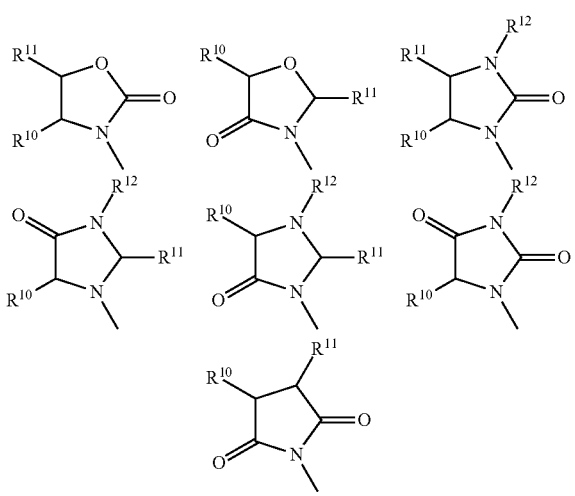

wherein $R^{10}$, $R^{11}$, and $R^{12}$ are as defined herein.

In another aspect, compounds of formulae (I), (II), or (III) are described, wherein $R^3$ is a structure selected from the group consisting of

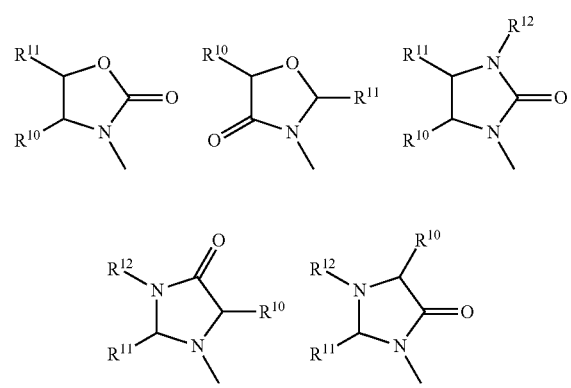

where $R^{10}$, $R^{11}$, and $R^{12}$ are as defined herein.

In another aspect, compounds of formulae (I), (II), or (III) are described, wherein $R^3$ is a structure selected from the group consisting of

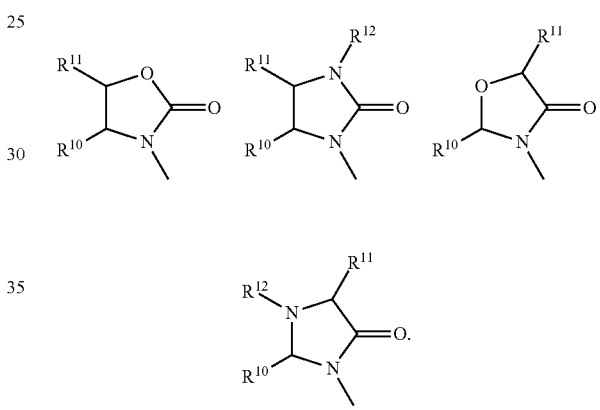

where $R^{10}$, $R^{11}$, and $R^{12}$ are as defined herein.

It is to be understood that the foregoing embodiments, aspects, and variations of the invention described herein may be combined in all possible ways to define additional embodiments, aspects, and variations. For example, in another aspect, formulae (I), (II), or (III) are described wherein A is a disubstituted amino having the formula $R^{14}XN-$, where $R^{14}$ and X are taken together with the attached nitrogen atom to form piperidinyl optionally substituted in the 4-position with alkyl, including $C_1$-$C_4$ alkyl, or heterocyclyl($C_1$-$C_4$ alkyl); and $R^3$ is the structure

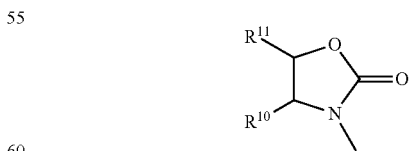

wherein $R^{10}$ and $R^{11}$ are as defined herein.

The compounds described herein possess an azetidinone core structure that includes asymmetric carbon atoms at C(3) and C(4), creating four stereoisomeric configurations, as illustrated by the following:

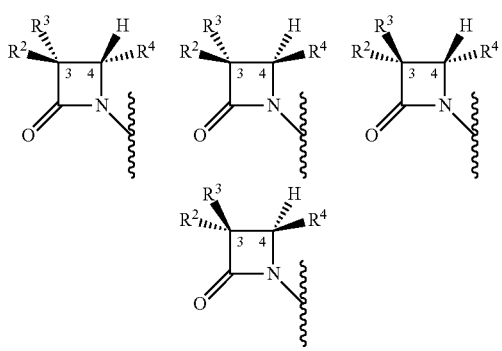

The compounds described herein may therefore exist as single diastereomers, as a racemic mixture, or as a mixture of various diastereomers. It is understood that in some applications, certain stereoisomers or mixtures of stereoisomers may be used, while in others applications, other stereoisomers or mixtures of stereoisomers may be used. In some embodiments, a single stereoisomer is described, such as the azetidinone core structure having the (3S,4R)-diastereomeric configuration.

It is also understood that the α-carbon bearing $R^1$ is also chiral. Furthermore, the groups selected for $R^1$, $R^2$, $R^3$, $R^4$, and A may also include chiral centers. For example, when $R^3$ is 4-substituted oxazolidin-2-on-3-yl, the 4-position of that ring is asymmetric. In addition, when $R^3$ is 2,5-disubstituted oxazolidin-4-on-3-yl or 1,2,5-trisubstituted imidazolidin-4-on-3-yl, the 2- and 5-carbons of those rings are each asymmetric. Finally, when $R^3$ is succinimido and one of $R^{14}$ and $R^{15}$ is hydrogen, the carbon bearing the non-hydrogen substituent is also asymmetric. Therefore, additional stereoisomers are collectively represented by formulae (I), (II), or (III). While compounds possessing all combinations of stereochemical purity are contemplated by the present description, it is appreciated that in many cases at least one of these chiral centers described above may be present as a single absolute configuration in a compound described herein. In one illustrative aspect, the compounds described herein have the (αR,3S,4R) absolute configuration or the (αS,3S,4R) absolute configuration.

Illustrative embodiments of the compounds described herein include classes of compounds of formulae (I), (II), or (III) where:

A is $R^5O$—;
A is $R^5O$—, and $R^5$ is $C_1$-$C_6$ alkyl;
A is $R^5O$—, and $R^5$ is optionally substituted aryl($C_1$-$C_4$ alkyl);
A is a monosubstituted amino of the formula XNH—;
A is a disubstituted amino having the formula $R^{14}$XN—;
A is XNH— or $R^{14}$XN, and X is optionally substituted aryl($C_1$-$C_4$ alkyl);
A is XNH— or $R^{14}$XN, and X is $R^6R^7$N—($C_1$-$C_4$ alkyl);
A is XNH— or $R^{14}$XN, X is $R^6R^7$N—($C_1$-$C_4$ alkyl), and $R^6$ and $R^7$ are taken together with the attached nitrogen atom to form an heterocycle;
A is $R^{14}$XN, and $R^{14}$ and X are taken together with the attached nitrogen atom to form an heterocycle;
A is $R^{14}$XN, $R^{14}$ and X are taken together with the attached nitrogen atom to form an heterocycle, and the heterocycle is optionally substituted with an optionally substituted heterocyclyl($C_1$-$C_4$ alkyl);
A is $R^{14}$XN, $R^{14}$ and X are taken together with the attached nitrogen atom to form a piperadinyl, and the piperadinyl is optionally substituted in the 4-position with heterocyclyl($C_1$-$C_4$ alkyl), including piperadinyl($C_1$-$C_4$ alkyl), piperazinyl($C_1$-$C_4$ alkyl), and pyrrolidinyl($C_1$-$C_4$ alkyl);
A is XNH— or $R^{14}$XN—, and X is optionally substituted aryl($C_1$-$C_4$ alkyl);
A is XNH— or $R^{14}$XN—, X is optionally substituted aryl($C_1$-$C_4$ alkyl), and aryl is optionally substituted phenyl;
$R^1$ is hydrogen;
$R^1$ is $C_1$-$C_6$ alkyl;
$R^1$ is $C_1$-$C_2$ alkyl;
$R^2$ is hydrogen;
$R^2$ is $C_1$-$C_2$ alkyl;
$R^2$ is methyl;
$R^2$ is methylthio;
$R^2$ is cyano;
$R^3$ is 4-substituted oxazolidin-2-on-3-yl;
$R^3$ is 4,5-disubstituted oxazolidin-2-on-3-yl;
$R^3$ is 2-substituted oxazolidin-4-on-3-yl;
$R^3$ is 2-substituted imidazolidin-4-on-3-yl;
$R^3$ is 1,2-disubstituted imidazolidin-4-on-3-yl;
$R^3$ is 5-substituted imidazolidin-2-on-1-yl;
$R^3$ is 4,5-disubstituted imidazolidin-4-on-1-yl;
$R^4$ is optionally substituted 2-aryleth-1-yl;
$R^4$ is optionally substituted 2-arylethen-1-yl;
$R^{5'}$ is $C_1$-$C_6$ alkyl;
$R^{5'}$ is optionally substituted aryl($C_1$-$C_4$ alkyl);

Further illustrative embodiments of the compounds described herein include classes of compounds of formula (II) where A, $R^5$, X, $R^{14}$, $R^1$, $R^2$, $R^3$, and $R^4$ are as described above; and where Aryl is phenyl, substituted phenyl, or 4-substituted phenyl.

It is appreciated that the classes of compounds described above may be combined to form additional illustrative classes. Further combinations of the classes of compounds described above are contemplated in the present invention.

Further illustrative classes of compounds are described by the following formula:

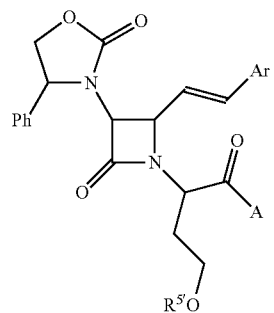

wherein Ar is optionally-substituted phenyl, optionally-substituted pyridinyl, optionally-substituted furyl, or optionally-substituted thienyl; A is nitrogen-containing heterocycle attached at the nitrogen atom, which is optionally substituted with heterocyclyl($C_1$-$C_4$ alkyl); and $R^{5'}$ is optionally substituted arylalkyl, including aryl($C_1$-$C_4$ alkyl).

Further illustrative classes of compounds are described by the

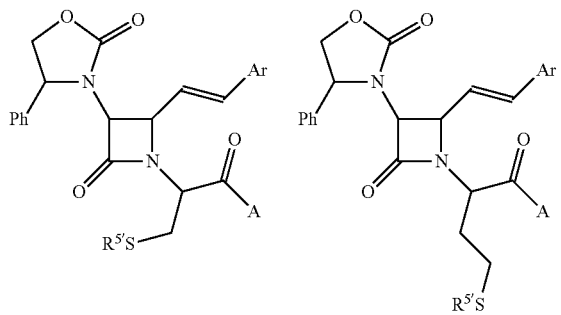

wherein Ar is optionally-substituted phenyl, optionally-substituted pyridinyl, optionally-substituted furyl, or optionally-substituted thienyl; A is nitrogen-containing heterocycle attached at the nitrogen atom, which is optionally substituted with heterocyclyl($C_1$-$C_4$ alkyl); and $R^{5'}$ is optionally substituted arylalkyl, including aryl($C_1$-$C_4$ alkyl).

Further illustrative classes of compounds are described by compounds of the following formula

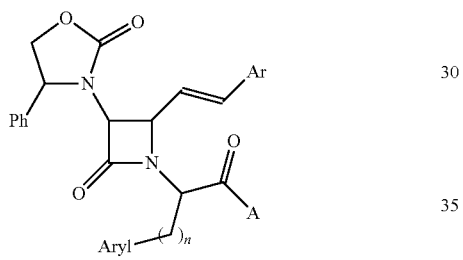

wherein Ar is optionally-substituted phenyl, optionally-substituted pyridinyl, optionally-substituted furyl, or optionally-substituted thienyl; A is nitrogen-containing heterocycle attached at the nitrogen atom, which is optionally substituted with heterocyclyl($C_1$-$C_4$ alkyl); n is 1, 2, or 3; and Aryl is optionally substituted phenyl or optionally substituted naphthyl.

In another embodiment, the compounds described herein include a basic amino group. Such amines are capable of forming salts with a variety of inorganic and organic acids to form pharmaceutically acceptable acid addition salts. It is appreciated that in cases where compounds of the formulae described herein are oils rather than solids, those compounds capable of forming addition salts that are solid will ease the handling and administration of the compounds described herein. Acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid, trifluoroacetic acid, maleic acid or fumaric acid.

The compounds described herein are useful in methods for antagonism of the vasopressin $V_{1a}$, $V_{1b}$, and $V_2$ receptors. Such antagonism is useful in treating a variety of disorders and diseases that have been linked to this receptor in mammals. Illustratively, the mammal to be treated by the administration of compounds described herein is human.

In another embodiment, compounds are also described herein that cross the blood brain barrier. It is appreciated that compounds that cross the blood brain barrier may have wider application in treating various disease states that are responsive to vasopressin antagonism. For example, it is to be understood that there are currently recognized distinct subtypes within depressive illness.

In another embodiment, processes for preparing compounds of formulae (I), (II), or (III) are described. In one aspect, processes for preparing compounds of the formulae:

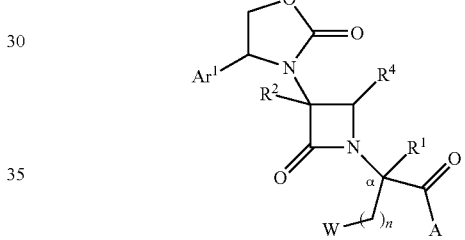

are described, wherein W is $QR^{5'}$ or Aryl as described in various embodiments herein; $Ar^1$ is optionally substituted aryl, or optionally substituted heteroaryl; and $R^1$, $R^2$, $R^4$, n, and A, are as described in various embodiments herein. The processes include the step of reacting a compound of the formula:

(A)

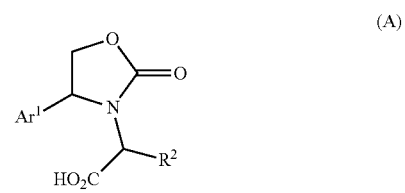

with a compound of the formula:

(B)

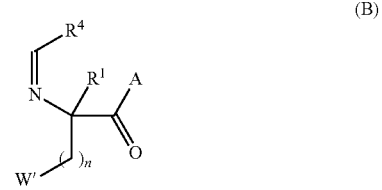

wherein W' is -QR$^5$ or Aryl as described in various embodiments herein, or W' is a protected form of QR$^{5'}$ or Aryl that may be deprotected or converted into -QR$^{5'}$ or Aryl. In one aspect of the process, when Q is oxygen, n is 2. In one variation, processes for preparing compounds of the above formula, wherein R$^4$ is optionally substituted arylethenyl are described. The processes include the step of reacting a compound of the formula (A) with a compound of the formula:

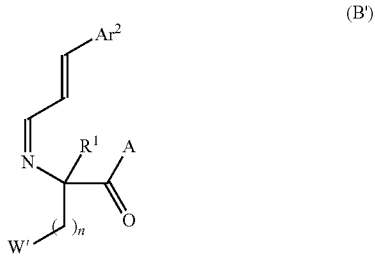

(B')

wherein W' is -QR$^{5'}$ or Aryl as described in various embodiments herein, or W' is a protected form of QR$^{5'}$ or Aryl that may be deprotected or converted into -QR$^{5'}$ or Aryl. In one aspect of the process, when Q is oxygen, n is 2.

Generally, the 2-(azetidinon-1-yl)acetic acid esters and amides, and the analogs and derivatives thereof described herein may be prepared by syntheses known in the art, as well as by the various methods described herein. As illustrated for compounds of formulae (I), (II), and (III), the 2-(azetidinon-1-yl)alkanedioic acid esters described herein are obtainable by the 2+2 cycloaddition of an appropriately substituted acetic acid derivative thereof (i), and an imine ester (ii) upon treatment with a base in an appropriately selected solvent, as described in Synthetic Scheme I, where Z is hydroxyl or a leaving group, and the integer n, and the moieties A, R$^1$, R$^2$, R$^3$, and R$^4$ are as previously described. The term "leaving group" as used hereinafter refers to a substitutent, such as halo, acyloxy, benzoyloxy and the like, present on an activated carbon atom that may be replaced by a nucleophile. The chemistry described in Synthetic Scheme I is applicable to imines (ii) bearing ester, thioester, or amide moieties.

The preparation of the appropriate imines (ii), preparation of representative examples of the required acetyl halides or anhydrides (i), and the cycloaddition procedure are generally described in U.S. Pat. Nos. 4,665,171 and 4,751,299, the disclosures of which are hereby incorporated by reference. It is appreciated that when Q is sulfur in compounds (ii-a), or an oxidized form thereof, such as sulfoxide or sulfone, certain reaction conditions may not be compatible. In those cases, appropriately selected protecting groups may be used to block unintended reactions of the sulfur. Illustrative sulfur protecting groups are described in Greene & Wuts "Protective Groups in Organic Synthesis," 2d Ed., John Wiley & Sons, New York, 1991, the disclosure of which is incorporated herein by reference.

In one illustrative variation, R$^3$ is a 4-substituted oxazolidin-2-on-3-yl or 1,4,5-trisubstituted imidazolidin-2-on-3-yl. Those compounds of formulae (I), (II), and (III) requiring R$^3$ to be a 4-substituted oxazolidin-2-on-3-yl or 1,4,5-trisubstituted imidazolidin-2-on-3-yl are prepared from the corresponding (4-substituted oxazolidin-2-on-3-yl) or (1,4,5-trisubstituted imidazolidin-2-on-3-yl)acetyl halide or anhydride. The acid halide or anhydride is available from an appropriately substituted glycine. The glycine is first converted to the carbamate and then reduced to provide the corresponding alcohol. The alcohol is then cyclized to the 4-substituted oxazolidin-2-one, which is subsequently N-alkylated with a haloacetic acid ester. The ester is hydrolyzed, and the resulting acid is converted to the acetyl halide or anhydride (i). Illustrative of the oxazolidinones that are included in this synthetic route, and subsequent synthetic routes described herein, include the following commercially available compounds.

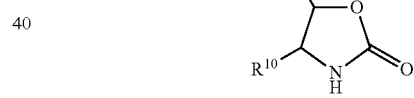

| R$^{10}$ | R$^{11}$ |
| --- | --- |
| (4R)-methyl | (5S)-phenyl |
| (4R)-methyl | diphenyl |
| (4S)-phenyl | (5R)-phenyl |
| (4S)-phenyl | diphenyl |
| (4S)-benzyl | dimethyl |
| (4S)-tert-butyl | diphenyl |
| (4R)-benzyl | H |
| (4R)-isopropyl | H |
| (4S)-methyl | (5R)-phenyl |
| (4R)-phenyl | (5S)-phenyl |
| (4S)-tert-butyl | H |
| (4S)-1H-indol-3-ylmethyl | H |
| (4S)-benzyl | H |
| (4S)-diphenylmethyl | H |
| (4S)-isopropyl | H |

Illustrative of the imidazolidinones and imidazolidindiones that are included in this synthetic route, and subsequent synthetic routes described herein, include the following commercially available compounds.

Snythetic Scheme I

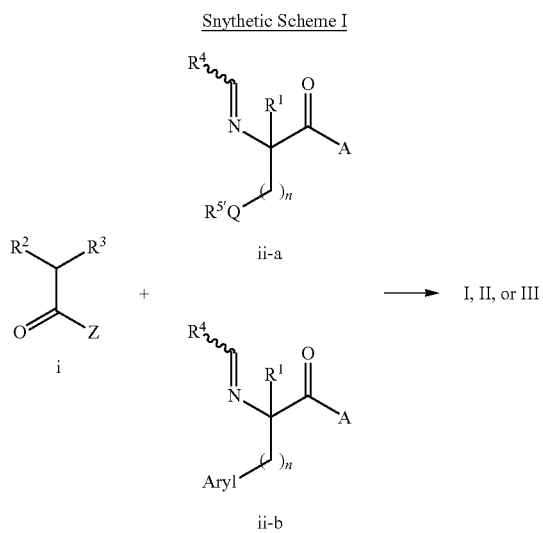

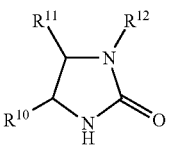

| $R^{10}$ | $R^{11}$ | $R^{12}$ |
|---|---|---|
| H | H | 2-methoxyphenyl |
| H | H | 4-methoxyphenyl |
| H | H | 2-methylphenyl |
| H | H | 3-methylphenyl |
| H | H | 4-methylphenyl |
| H | H | acetyl |
| H | H | phenyl |
| (4S)-phenyl | (5R)-methyl | methyl |
| H | H | methyl |
| H | H | tert-butyl |

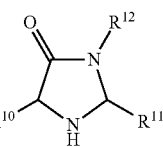

| $R^{10}$ | $R^{11}$ | $R^{12}$ |
|---|---|---|
| (5S)-benzyl | (2S)-tert-butyl dimethyl | (5S)-benzyl methyl |
| H | (2R)-tert-butyl | methyl |

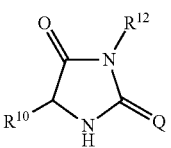

| $R^{10}$ | $R^{12}$ | Q |
|---|---|---|
| methyl | phenyl | S |

In another illustrative variation, $R^3$ is 2,5-disubstituted oxazolidin-4-on-3-yl or 1,2,5-trisubstituted imidazolidin-4-on-3-yl. Those compounds of formulae (I), (II), and (III) requiring $R^3$ to be 2,5-disubstituted oxazolidin-4-on-3-yl or 1,2,5-trisubstituted imidazolidin-4-on-3-yl are prepared from the corresponding (2,5-disubstituted oxazolidin-4-on-3-yl) or (1,2,5-trisubstituted imidazolidin-4-on-3-yl)acetyl chlorides or anhydrides respectively. Reaction conditions useful for preparing these reagents are described in U.S. Pat. No. 4,772,694, hereby incorporated by reference. Briefly, the required oxazolidinone or imidazolidinone is obtained from an α-hydroxyacid or an α-aminoacid, respectively. The imidazolones are prepared by converting the α-aminoacid, $(R^{11})$—$CH(NH_2)CO_2H$, to an amino-protected amide and then condensing the amide with an aldehyde, $(R^{10})$—CHO, in the presence of an acid to form the 3-protected imidazolidin-4-one, where $R^{10}$ and $R^{11}$ are as defined above. The 1-position may be functionalized with an appropriate reagent to introduce $R^{12}$ and the 3-position deprotected, where $R^{12}$ is as defined above. The imidazolidin-4-one ring is then alkylated with a haloacetic acid ester, the ester deesterified, and the resulting acetic acid converted to the desired acid halide or anhydride (i). The required oxazolidinones are prepared in an analogous manner from the corresponding α-hydroxyacid, $(R^{11})$—$CH(OH)CO_2H$.

In another illustrative variation, $R^3$ is succinimido. Those compounds of formulae (I), (II), and (III) requiring $R^3$ to be succinimido are prepared from the corresponding 2-(succinimido)acetyl halide or anhydride. The chemistry to prepare these reagents is described in U.S. Pat. No. 4,734,498, hereby incorporated by reference. Briefly, these reagents are obtained from tartaric acid or, when one of $R^{10}$ and $R^{11}$ is hydrogen, from malic acid. Tartaric acid is acylated or O-alkylated, the corresponding diacyl or di-O-alkyl tartaric acid is treated with an acid anhydride to form the succinic anhydride, and reaction of this succinic anhydride with an ester of glycine to form first the noncyclic half amide ester which is then cyclized to the 3,4-disubstituted succinimidoacetic acid ester. The ester group is deesterified and the resulting acid converted to the corresponding acid halide or anhydride (1). The mono-substituted succinimidoacetyl halide or anhydride is obtained with malic acid via succinic anhydride formation followed by succinimide formation as described above.

In another illustrative variation, $R^3$ is an N-substituted amine or an N'-substituted urea. Those compounds of formulae (I), (II), and (III) requiring $R^3$ to be an N-substituted amine or an N'-substituted urea may be prepared from the corresponding phthalimido protected 3-amino analogs. The phthalimide protecting group may be removed using conventional procedures, such as by treatment with hydrazine, and the like. Once liberated, the amine may be alkylated with any one of a variety of alkyl and cycloalkyl halides and sulfates, such as methyl iodide, isopropylbromide, diethyl sulfate, cyclopropylmethylbromide, cyclopentyliodide, and the like. Such amines may also be acylated with acid halides, acid anhydrides, isocyanates, isothiocyanates, such as acetyl chloride, propionic anhydride, methylisocyanate, 3-trifluoromethylphenylisothiocyanate, and the like.

The bases to be used in Synthetic Scheme I include, among others, aliphatic tertiary amines, such as trimethylamine and triethylamine, cyclic tertiary amines, such as N-methylpiperidine and N-methylmorpholine, aromatic amines, such as pyridine and lutidine, and other organic bases such as 1,8-diazabicyclo[5,4,0]undec-7-ene (DBU).

The solvents useful for reactions described in Synthetic Scheme I include, among others, dioxane, tetrahydrofuran, diethyl ether, ethyl acetate, dichloromethane, chloroform, carbon tetrachloride, benzene, toluene, acetonitrile, dimethyl sulfoxide and N,N-dimethylformamide. It is appreciated that any desired stereochemical configuration of these compounds may be prepared using the processes described herein, by selecting the desired configuration at each chiral center noted above. Such a selection may be accomplished by using optically pure starting materials, or by separating mixtures of optical isomers at convenient times during the syntheses of the two foregoing formulae using standard techniques.

The azetidinone ring may also be prepared with a deficit of substituents $R^2$, $R^3$, $R^4$, or the $R^1$-substituted N-alkanedioic acid or alkoxyalkanoic acid moiety, but possessing substituents capable of being elaborated through subsequent chemical transformation to such groups described for compounds of formulae (I), (II), and (III). In general, azetidinones may be prepared via N—C(4) cyclization, such as the cyclization of acylhydroxamates (iv) to azetidinone intermediates (v), as depicted in Scheme II, and illustrated for compounds of formula (I), where $R^1$, $R^2$, $R^3$, $R^4$, and A are as defined above, according to the procedure of Mattingly et al., in *J. Am. Chem. Soc.* (1979), 101, 3983 and *Accts. Chem. Res.* (1986), 19, 49, the disclosures of which are incorporated herein by reference. It is appreciated that other hydroxamates, such as alkylhydroxamates, aryl hydroxamates, and the like, are suitable for carrying out the cyclization.

Synthetic Scheme II

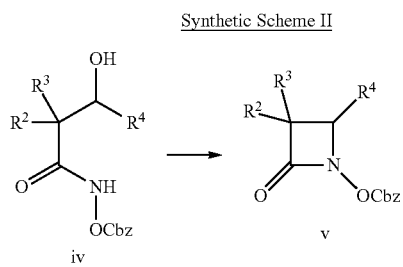

Subsequent chemical transformation of the acyloxyazetidinone (v) to introduce for example an $R^1$-substituted amino acid imine using conventional procedures will illustratively provide compounds of formulae (I), (II), and (III).

An alternative cyclization to form intermediate azetidinones, which may be further elaborated to compounds of formulae (I), (II), and (III) may occur by oxidative cyclization of acylhydroxamates (vi) to intermediate azetidinones (vii), as illustrated in Synthetic Scheme III, and illustrated for compounds of formula (I), where $R^2$ and $R^3$ are as defined above and L is a leaving group such as halide, according to the procedure of Rajendra and Miller in *J. Org. Chem.* (1987), 52, 4471 and *Tetrahedron Lett.* (1985), 26, 5385, the disclosures of which are incorporated herein by reference. The group R in Scheme III represents an alkyl or aryl moiety selected to provide $R^4$, as defined above, upon subsequent transformation. For example, R may be the group $ArCH_2$— where Ar is an optionally substituted aryl group, as in (vii-a), such that oxidative elimination of HBr will provide the desired $R^4$, such as a styryl group, as in (vii-b). It is appreciated that elaboration of R to $R^4$ is not necessarily performed immediately subsequent to the cyclization and may be performed conveniently after other steps in the synthesis of compounds of formulae (I), (II), and (III). It is further appreciated that alternatives to the acylhydroxamates shown, such as alkylhydroxamates, aryl hydroxamates, and the like, are suitable for carrying out the cyclization.

Synthetic Scheme III

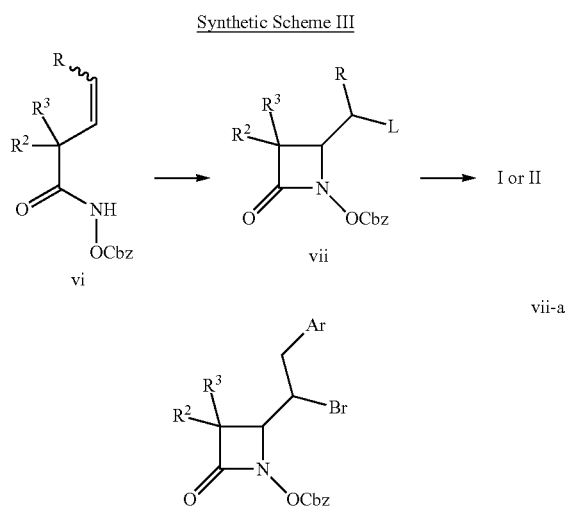

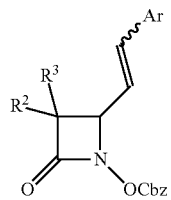

Still other useful intermediates, such as the azetidinonyl acetic acid derivatives (x), may be converted into compounds of formulae (I), (II), and (III), as illustrated for the synthesis of compounds of formula (I) in Synthetic Scheme IV, and illustrated for compounds of formula (I), where $R^1$, $R^2$, $R^3$, $R^4$, A, and n are as defined above. Introduction of the $R^1$ moiety, and a carboxylic acid derivative $R^{5'}$-Q-$(CH_2)_n$— for compounds of formula (I), may be accomplished by alkylation of the anion of (x).

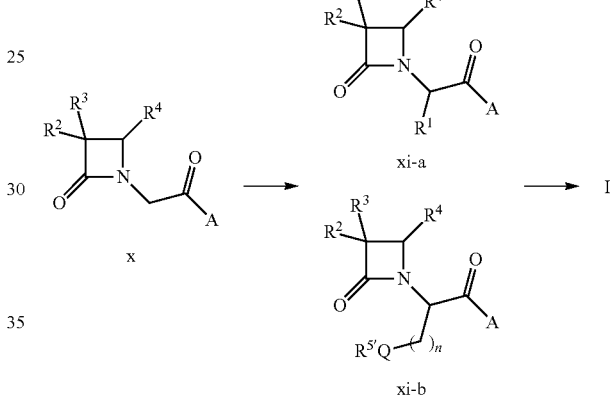

Acetic acid derivative (x) is deprotonated and subsequently alkylated with an alkyl halide corresponding to $R^1$—Z, where Z is a leaving group, to provide intermediate (xi-a). Illustratively, the anion of (xi-a) may be alkylated with a compound Z'—$(CH_2)_n QR^{5'}$, where Z' is a leaving group, to provide compounds of formula (I).

A solution of the 2-(3,4-disubstituted azetidin-2-on-1-yl) acetic acid derivative (x) or (xi) in an appropriate solvent, such as tetrahydrofuran, dioxane, or diethyl ether, is treated with a non-nucleophilic base to generate the anion of (x) or (xi), respectively. Suitable bases for this transformation include lithium diisopropylamide, lithium 2,2,6,6-tetramethylpiperidinamide, or lithium bis(trimethylsilyl)amide. The anion is then reacted with an appropriate electrophile to provide the desired compounds. Illustrative electrophiles represented by the formula Aryl-$(CH_2)_n$—Z provide the corresponding compounds.

The foregoing synthetic procedures may be used generally for the preparation of the compounds described herein, including but not limited to the serine, homoserine, cysteine, homocysteine, phenylalanine, homophenylalanine, and further homologs thereof. In addition, those same synthesis may be used to prepare analogs and derivatives of thereof, such as tyrosine analogs, naphthyl and substituted naphthyl analogs, oxidized embodiments of the sulfur containing compounds, disulfide embodiments of the sulfur containing compounds, oxidized disulfide embodiments of the sulfur containing compounds, and the like.

Alternatively, disulfide embodiments may be prepared from serine and homoserine compounds by converting the terminal hydroxyl group into a leaving group, such as a halo, alkyl or arylsulfonyl, acyloxy, and the like to prepare the compounds of formula (I) or (III), as shown in Scheme V and illustrated for compounds of formula (I).

Synthetic Scheme V

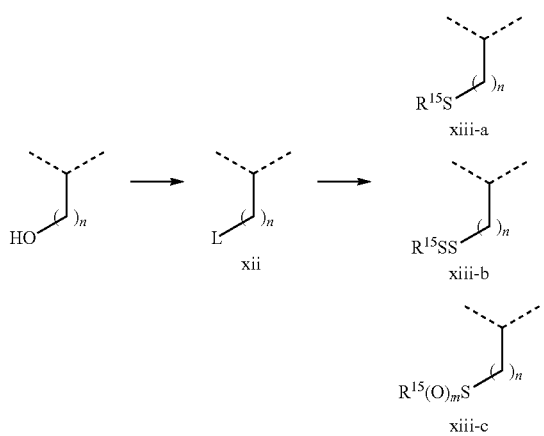

Serine and homoserine compounds may converted into compounds of formula (xii), where L is a leaving group using conventional processes. Compounds (xii) may then be converted in compounds (xiii) by treating with a sulfide anion, disulfide anion, sulfoxide anion, or sulfonyl anions, wherein $R^{15}$ is as defined herein, and m is 1 or 2. It is appreciated that other nucleophiles, including sulfonylthio may also be used to displace the leaving group L in the preparation of compounds (xiii).

Alternatively, oxidized sulfur atoms may be synthesized by nucleophilic displacement treatment of the thioether or disulfide compounds described herein by treating with an oxidizing agent, such as a peroxy-based oxidizing agent, and the like. Typical oxidizing agents include hydrogen peroxide, peroxides, peroxy acids, and the like. In the case of disulfide oxidation, it is appreciated that only one of the two sulfur atoms may undergo oxidation. It is further appreciated that under such circumstances, the sulfur atom adjacent to the more electron-donating group may be selectively oxidized.

Alternatively, oxidized sulfur atoms may be synthesized by conventional treatment of the thioether or disulfide compounds described herein by treating with an oxidizing agent, such as a peroxy-based oxidizing agent, and the like. Typical oxidizing agents include hydrogen peroxide, peroxides, peroxy acids, and the like. In the case of disulfide oxidation, it is appreciated that only one of the two sulfur atoms may undergo oxidation. It is further appreciated that under such circumstances, the sulfur atom adjacent to the more electron-donating group may be selectively oxidized.

The compounds prepared as described in Synthetic Schemes I-V may be pure diastereomers, mixtures of diastereomers, or racemates. The actual stereochemical composition of the compound will be dictated by the specific reaction conditions, combination of substituents, and stereochemistry or optical activity of the reactants employed. It is appreciated that diasteromeric mixtures may be separated by chromatography or fractional crystallization to provide single diastereomers if desired, using standard methods. Particularly, the reactions described in Synthetic Schemes II, III, and IV create a new chiral center at the carbon bearing $R^1$.

Alternative syntheses have also been described, including the syntheses of several members of the structural class of substituted 2-(azetidin-2-on-1-yl)acetic acid esters and amides for the preparation of β-lactam antibiotics. See, e.g., U.S. Pat. No. 4,751,299.

The following preparations and examples further illustrate the compounds that are illustrative of the invention described herein, including the synthesis of such compounds, but such exemplary preparations and examples and are not intended to and should not be interpreted to limit the scope of the invention in any way. Unless otherwise indicated, all reactions were performed at ambient temperature, and all evaporations were performed in vacuo. All of the compounds described below were characterized by standard analytical techniques, including nuclear magnetic resonance spectroscopy (NMR) and mass spectral analysis (MS).

EXAMPLES

Each of the Examples prepared below exhibited an $^1$H NMR spectrum consistent with the assigned structure. Mass spectral analysis was also performed using FAB$^+$ to observe the corresponding (M+H)$^+$ parent ion.

Example 1A (4(S)-phenyloxazolidin-2-on-3-yl)acetyl chloride A solution of 1.0 equivalent of (4(S)-phenyloxazolidin-2-on-3-yl) acetic acid (Evans, U.S. Pat. No. 4,665,171) and 1.3 equivalent of oxalyl chloride in 200 mL dichloromethane was treated with a catalytic amount of anhydrous dimethylformamide (85 μL/milliequivalent of acetic acid derivative) resulting in vigorous gas evolution. After 45 minutes all gas evolution had ceased and the reaction mixture was concentrated under reduced pressure to provide the title compound as an off-white solid after drying for 2 h under vacuum.

Example 1B (4(R)-phenyloxazolidin-2-on-3-yl)acetyl chloride.
Prepared following the procedure of Example 1A, except that (4(R)-phenyloxazolidin-2-on-3-yl)acetic acid was used instead of (4(S)-phenyloxazolidin-2-on-3-yl)acetic acid (see, Evans & Sjogren, Tetrahedron Lett. 26:3783 (1985)).

Example 1C.

2-(4(S)-Phenyloxazolidin-2-on-3-yl)propanoyl Chloride. A solution of 1 equivalent of Example 3A and 1.3 equivalent of oxalyl chloride in 200 mL CH$_2$Cl$_2$ (150 mL/g of propanoic acid derivative) was treated with a catalytic amount of anhydrous DMF (85 μL/mmole of propanoic acid derivative) resulting in vigorous gas evolution. After 45 min., all gas evolution had ceased and the reaction mixture was concentrated under reduced pressure to provide the title compound as an off-white solid after drying for 2 h. under vacuum.

Example 2A

Methyl (4(S)-phenyloxazolidin-2-on-3-yl)acetate. A solution of (4(S)-phenyloxazolidin-2-on-3-yl)acetic acid (1 g, 4.52 mmol) (Evans in U.S. Pat. No. 4,665,171) in 20 mL of anhydrous methanol was treated hourly with 5 equivalents of acetyl chloride, for a total of 20 equivalents. The resulting solution was stirred overnight. The residue obtained after evaporation of the MeOH was redissolved in 30 mL of CH$_2$Cl$_2$ and treated with 50 mL of saturated aqueous Na$_2$CO$_3$. The organic layer was evaporated and dried (MgSO$_4$) to yield the title compound as a colorless oil (1.001 g, 94%); $^1$H NMR (CDCl$_3$) δ 3.37 (d, J=18.0 Hz, 1H), 3.69 (s, 3H), 4.13 (t, J=8.3 Hz, 1H), 4.28 (d, J=18.0 Hz, 1H), 4.69 (t, J=8.8 Hz, 1H), 5.04 (t, J=8.4 Hz, 1H), 7.26-7.29 (m, 2H), 7.36-7.42 (m, 3H).

Example 2B

Methyl 2-(4(S)-phenyloxazolidin-2-on-3-yl)propanoate. A solution of Example 2A (1 g, 4.25 mmol) in 10 mL of anhydrous THF at −78° C. was treated with 4.68 mL (4.68 mmol) of a 1 M solution of lithium bis(trimethylsilyl)amide in THF. The reaction mixture was stirred for 1 h. at about −70° C. before adding MeI (1.59 mL, 25.51 mmol). Upon complete conversion of the azetidinone, the reaction was quenched with saturated aqueous NH$_4$Cl and partitioned between EtOAc and water. The organic layer was washed sequentially with saturated aqueous sodium bisulfite, and saturated aqueous NaCl. The resulting organic layer was dried (MgSO$_4$) and evaporated to afford the title compound (a mixture of diastereomers) as a white solid (1.06 g, 93%); $^1$H NMR (CDCl$_3$) δ 1.07/1.53 (d/d, J=7.5 Hz, 3H), 3.59/3.74 (s/s, 3H), 3.85/4.48 (q/q, J=7.5 Hz, 1H), 4.10-4.14 (m, 1H), 4.60-4.64/4.65-4.69 (m/m, 1H), 4.88-4.92/4.98-5.02 (m/m, 1H), 7.24-7.40 (m, 5H).

Example 3A 2-(4(S)-Phenyloxazolidin-2-on-3-yl)propanoic acid.
To a solution of Example 2B (1 g, 4.01 mmol) in 35 mL of MeOH was added, at 0° C., 14.3 mL (12.04 mmol) of a 0.84 M solution of LiOH in water. The reaction mixture was then stirred for 3 h. at ambient temperature. Upon complete hydrolysis of the azetidinone, the MeOH was removed by evaporation, the crude residue dissolved in CH$_2$Cl$_2$ and treated with saturated aqueous NaCl. The resulting organic layer was dried (MgSO$_4$) and evaporated to afford the title compound (racemic mixture) as a white solid (0.906 g, 96%); $^1$H NMR (CDCl$_3$) δ1.13/1.57 (d/d, J=7.5 Hz, 3H), 3.75/4.50 (q/q, J=7.5 Hz, 1H), 4.10-4.16 (m, 1H), 4.62-4.72 (m, 1H), 4.92-5.03 (m, 1H), 7.32-7.43 (m, 5H).

Example 4

General procedure for amide formation from an activated ester derivative. N-Benzyloxycarbonyl-L-aspartic acid β-t-butyl ester α-(3-trifluoromethyl)benzylamide. A solution of N-benzyloxycarbonyl-L-aspartic acid β-t-butyl ester α-N̄-hydroxysuccinimide ester (1.95 g, 4.64 mmol, Advanced ChemTech) in 20 mL of dry tetrahydrofuran was treated with 0.68 mL (4.74 mmol) of 3-(trifluoromethyl)benzyl amine. Upon completion (TLC, 60:40 hexanes/ethyl acetate), the mixture was evaporated, and the resulting oil was partitioned between dichloromethane and a saturated aqueous solution of sodium bicarbonate. The organic layer was evaporated to give 2.23 g (quantitative yield) of the title compound as a white solid; $^1$H NMR (CDCl$_3$) δ 1.39 (s, 9H), 2.61 (dd, J=6.5 Hz, J=17.2 Hz, 1H), 2.98 (dd, J=3.7 Hz, J=17.0 Hz, 1H), 4.41 (dd, J=5.9 Hz, J=15.3 Hz, 1H), 4.50-4.57 (m, 2H), 5.15 (s, 2H), 5.96-5.99 (m, 1H), 6.95 (s, 1H), 7.29-7.34 (m, 5H), 7.39-7.43 (m, 2H), 7.48-7.52 (m, 2H).

Example 5

General procedure for hydrolysis of a tert-butyl ester. A solution of tert-butyl ester derivative in formic acid, typically 1 g in 10 mL, is stirred at ambient temperature until no more ester is detected by thin layer chromatography (dichloromethane 95%/methanol 5%), a typical reaction time being around 3 hours. The formic acid is evaporated under reduced pressure; the resulting solid residue is partitioned between dichloromethane and saturated aqueous sodium bicarbonate. The organic layer is evaporated to give an off-white solid that may be used directly for further reactions, or recrystallized from an appropriate solvent system if desired.

Example 6

General procedure for amide formation from a carboxylic acid.Illustrated for N-Benzyloxycarbonyl-D-aspartic acid β-t-butyl ester α-(3-trifluoromethyl)benzylamide. A solution of 1 g (2.93 mmol) of N-benzyloxycarbonyl-D-aspartic acid β-t-butyl ester monoh̄ȳdrate (Novabiochem) in 3-4 mL of dichloromethane was treated by sequential addition of 0.46 mL (3.21 mmol) of 3-(trifluoromethyl)benzylamine, 0.44 g (3.23 mmol) of 1-hydroxy-7-benzotriazole, and 0.62 g (3.23 mmol) of 1-[3-(dimethylamino)propyl]-3-ethylcarbodiimide hydrochloride. After at least 12 hours at ambient temperature or until complete as determined by thin layer chromatography (95:5 dichloromethane/methanol eluent), the reaction mixture was washed sequentially with a saturated aqueous sodium bicarbonate solution and with distilled water. The organic layer was evaporated to give 1.41 g (quantitative yield) of the title compound as an off-white solid; $^1$H NMR (CDCl$_3$) δ 1.39 (s, 9H); 2.61 (dd, J=6.5 Hz, J=17.2 Hz, 1H); 2.98 (dd, J=4.2 Hz, J=17.2 Hz, 1H); 4.41 (dd, J=5.9 Hz, J=15.3 Hz, 1H); 4.50-4.57 (m, 2H); 5.10 (s, 2H); 5.96-6.01 (m, 1H); 6.91-7.00 (m, 1H); 7.30-7.36 (m, 5H); 7.39-7.43 (m, 2H); 7.48-7.52 (m, 2H).

Example 6A

N-tButyloxycarbonyl-(S)-(benzyl)-D-cysteine-[4-(2-(1-piperidyl)ethyl)]piperidinenamide. N-t-Butyloxycarbonyl-(S)-Benzyl-D-cysteine (0.289 g, 0.93 mmole) and 4-[2-(1-piperidyl)ethyl]piperidine (0.192 g, 0.98 mmole) were combined in dichloromethane (20 mL) according to the procedure of Example 6 to give 0.454 g (quantitative yield) as an off-white solid. $^1$H NMR (CDCl$_3$) δ 0.89-1.15 (m, 2H); 1.39-1.44 (m, 16H); 1.54-1.61 (m, 4H); 1.62-1.71 (m, 1H); 2.21-2.35 (m, 5H); 2.49-2.58 (m, 2H); 2.66-2.74 (m, 1H); 2.79-2.97 (m, 1H); 3.67-3.76 (m, 3H); 4.48-4.51 (m, 1H); 4.72-4.75 (m, 1H); 5.41-5.44 (m, 1H); 7.19-7.34 (m, 5H).

Example 7A

N-[(9H-Fluoren-9-yl)methoxycarbonyl]-O-(benzyl)-D-serine t-Butyl ester. N-[(9H-Fluoren-9-yl)methoxycarbonyl]-O-(benzyl)-D-serine (0.710 g, 1.70 mmole) in dichloromethane (8 mL) was treated with t-butyl acetate (3 mL) and concentrated sulfuric acid (40 µL) in a sealed flask at 0° C. Upon completion (TLC), the reaction was quenched with of dichloromethane (10 mL) and saturated aqueous potassium bicarbonate (15 mL). The organic layer was washed with distilled water, and evaporated. The resulting residue was purified by flash column chromatography (98:2 dichloromethane/methanol) to yield 0.292 g (77%) as a colorless oil; $^1$H NMR (CDCl$_3$) δ 1.44 (s, 9H); 3.68 (dd, J=2.9 Hz, J=9.3 Hz, 1H); 3.87 (dd, J=2.9 Hz, J=9.3 Hz, 1H); 4.22 (t, J=7.1 Hz, 1H); 4.30-4.60 (m, 5H); 5.64-5.67 (m, 1H); 7.25-7.39 (m, 9H); 7.58-7.61 (m, 2H); 7.73-7.76 (m, 2H).

Example 8A

O-(Benzyl)-D-serine t-Butyl ester. Example 7A (0.620 g, 1.31 mmol) in dichloromethane (5 mL) was treated with tris(2-aminoethyl)amine (2.75 mL) for 5 h. The resulting mixture was washed twice with a phosphate buffer (pH=5.5), once with saturated aqueous potassium bicarbonate, and evaporated to give 0.329 g (quantitative yield) of the title compound as an off-white solid; $^1$H NMR (CD$_3$OD) δ 1.44 (s, 9H); 3.48 (dd, J=J'=4.2 Hz, 1H); 3.61 (dd, J=4.0 Hz, J=9.2 Hz, 1H); 3.72 (dd, J=4.6 Hz, J=9.2 Hz, 1H); 4.47 (d, J=12.0 Hz, 1H); 4.55 (d, J=12.0 Hz, 1H); 7.26-7.33 (m, 5H).

Example 9

General Procedure for Formation of a 2-Azetidinone from an Imine and an acetyl chloride.

Step 1: General procedure for formation of an imine from an amino acid derivative. A solution of 1 equivalent of an α-amino acid ester or amide in dichloromethane is treated sequentially with 1 equivalent of an appropriate aldehyde, and a dessicating agent, such as magnesium sulfate or silica gel, in the amount of about 2 grams of dessicating agent per gram of starting α-amino acid ester or amide. The reaction is stirred at ambient temperature until all of the reactants are consumed as measured by thin layer chromatography. The reactions are typically complete within an hour. The reaction mixture is then filtered, the filter cake is washed with dichloromethane, and the filtrate concentrated under reduced pressure to provide the desired imine that is used as is in the subsequent step.

Step 2: General procedure for the 2+2 cycloaddition of an imine and an acetyl chloride. A dichloromethane solution of the imine (10 mL dichloromethane/1 gram imine) is cooled to 0° C. To this cooled solution is added 1.5 equivalents of an appropriate amine, typically triethylamine, followed by the dropwise addition of a dichloromethane solution of 1.1 equivalents of an appropriate acetyl chloride, such as that described in Example 1A (10 mL dichloromethane/1 gm appropriate acetyl chloride). The reaction mixture is allowed to warm to ambient temperature over 1 h and is then quenched by the addition of a saturated aqueous solution of ammonium chloride. The resulting mixture is partitioned between water and dichloromethane. The layers are separated and the organic layer is washed successively with 1N hydrochloric acid, saturated aqueous sodium bicarbonate, and saturated aqueous sodium chloride. The organic layer is dried over magnesium sulfate and concentrated under reduced pressure. The residue may be used directly for further reactions, or purified by chromatography or by crystallization from an appropriate solvent system if desired.

Example 9A tert-Butyl (2R)-(Benzyloxymethyl)-2-[3(S)-(4(S)-phenyloxazolidin-2-on-3-yl)-4(R)-(2-styryl)azetidin-2-on-1-yl] acetate. The imine prepared from 0.329 g (1.31 mmol) of O-(benzyl)-D-serine t-butyl ester (Example 8A) and cinnamaldehyde was combined with 2-(4(S)-phenyloxazolidin-2-on-3-yl)acetyl chloride (Example 1A) according to the procedure of Example 9 to give 0.543 g (73%) after flash column chromatography purification (90:10 hexanes/ethyl acetate); $^1$H NMR (CDCl$_3$) δ 1.39 (s, 9H); 3.56 (dd, J=2.7 Hz, J=9.5 Hz, 1H); 3.82 (dd, J=4.8 Hz, J=9.5 Hz, 1H); 4.11 (t, J=8.3 Hz, 1H); 4.21-4.29 (m, 2H); 4.50-4.58 (m, 3H); 4.71-4.78 (m, 2H); 6.19 (dd, J=9.1 Hz, J=16.0 Hz, 1H); 6.49 (d, J=16.0 Hz, 1H); 7.07-7.11 (m, 1H); 7.19-7.40 (m, 14H).

Example 9B (2S)-(Benzylthiomethyl)-2-[3(S)-(4(S)-phenyloxazolidin-2-on-3-yl)-4(R)-(2-styryl)azetidin-2-on-1-yl]acetic acid N-[4-[2-(piperid-1-yl)ethyl]piperidin-1-yl]amide. The imine prepared from (S)-(benzyl)-D-cysteine-[4-(2-(1-piperidyl) ethyl)]piperidinenamide, dihydrochloride (Example 11A, 0.417 g, 0.90 mmole) and cinnamaldehyde, in the presence on triethylamine (0.26 mL, 1.87 mmoles), was combined with 2-(4(S)-phenyloxazolidin-2-on-3-yl)acetyl chloride (Example 1A) according to the procedure of Example 9 to give 0.484 g (76%) as an off-white solid after recrytallization from dichloromethane/hexanes. $^1$H NMR (CDCl$_3$) δ 0.89-1.06 (m, 2H); 1.40-1.44 (m, 5H); 1.57-1.67 (m, 6H); 2.25-2.43 (m, 6H); 2.45-2.59 (m, 2H); 2.71-2.88 (m, 2H); 3.55-3.70 (m, 3H); 4.11-4.17 (m, 1H); 4.37-4.47 (m, 2H); 4.54-4.61 (m, 1H); 4.64-4.69 (m, 1H); 4.76-4.84 (m, 2H); 6.05-6.19 (m, 1H); 6.66-6.71 (m, 1H); 7.12-7.40 (m, 15H).

Examples 9C-9AD shown in the following Table, may also be prepared using the procedures described herein by replacing the serine or cysteine derivative described above with the one corresponding to the compounds shown below.

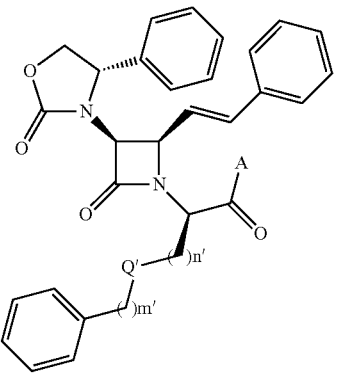

| Example | A | n' | Q' | m' |
|---|---|---|---|---|
| 9C | (3-trifluorobenzyl)amino | 2 | —O— | 1 |
| 9D | 4-(3-trifluoromethylphenyl)piperazin-1-yl | 2 | —O— | 2 |
| 9E | 4-(3-trifluoromethylphenyl)piperazin-1-yl | 2 | —O— | 1 |
| 9F | 4-cyclohexylpiperazin-1-yl | 2 | —O— | 2 |
| 9G | 4-(piperidin-1-ylmethyl)piperidin-1-yl | 2 | —O— | 1 |
| 9H | 4-(piperidin-1-yl)piperidin-1-yl | 2 | —O— | 2 |
| 9I | 4-[2-(piperidin-1-yl)ethyl]piperidin-1-yl | 2 | —O— | 1 |
| 9J | (3-trifluorobenzyl)amino | 1 | —S— | 2 |
| 9K | 4-(3-trifluoromethylphenyl)piperazin-1-yl | 1 | —S— | 1 |
| 9L | 4-(3-trifluoromethylphenyl)piperazin-1-yl | 1 | —S— | 2 |
| 9M | 4-cyclohexylpiperazin-1-yl | 1 | —S— | 1 |
| 9N | 4-(piperidin-1-ylmethyl)piperidin-1-yl | 1 | —S— | 2 |
| 9O | 4-(piperidin-1-yl)piperidin-1-yl | 1 | —S— | 1 |
| 9P | 4-[2-(piperidin-1-yl)ethyl]piperidin-1-yl | 1 | —S— | 2 |
| 9Q | (3-trifluorobenzyl)amino | 2 | —S— | 2 |
| 9R | 4-(3-trifluoromethylphenyl)piperazin-1-yl | 2 | —S— | 1 |
| 9S | 4-(3-trifluoromethylphenyl)piperazin-1-yl | 2 | —S— | 2 |
| 9T | 4-cyclohexylpiperazin-1-yl | 2 | —S— | 1 |
| 9U | 4-(piperidin-1-ylmethyl)piperidin-1-yl | 2 | —S— | 2 |
| 9V | 4-(piperidin-1-yl)piperidin-1-yl | 2 | —S— | 1 |
| 9W | 4-[2-(piperidin-1-yl)ethyl]piperidin-1-yl | 2 | —S— | 2 |
| 9X | (3-trifluorobenzyl)amino | 0 | —CH$_2$— | 1 |
| 9Y | 4-(3-trifluoromethylphenyl)piperazin-1-yl | 0 | —CH$_2$— | 2 |
| 9Z | 4-(3-trifluoromethylphenyl)piperazin-1-yl | 0 | —CH$_2$— | 1 |
| 9AA | 4-cyclohexylpiperazin-1-yl | 0 | —CH$_2$— | 2 |
| 9AB | 4-(piperidin-1-ylmethyl)piperidin-1-yl | 0 | —CH$_2$— | 1 |
| 9AC | 4-(piperidin-1-yl)piperidin-1-yl | 0 | —CH$_2$— | 2 |
| 9AD | 4-[2-(piperidin-1-yl)ethyl]piperidin-1-yl | 0 | —CH$_2$— | 1 |

Example 10A (2R)-(Benzyloxymethyl)-2-[3(S)-(4(S)-phenyloxazolidin-2-on-3-yl)-4(R)-(2-styryl)azetidin-2-on-1-yl]acetic acid. Example 9A (0.16 g, 0.28 mmol) was hydrolyzed according to the procedure used in Example 5 to give 0.144 g (quantitative yield) as an off-white solid; $^1$H NMR (CDCl$_3$) δ 3.65 (dd, J=4.0 Hz, J=9.5 Hz, 1H); 3.82 (dd, J=5.5 Hz, J=9.5 Hz, 1H); 4.11 (dd, J=7.8 Hz, J=8.8 Hz, 1H); 4.33 (s, 2H); 4.50 (d, J=5.0 Hz, 1H); 4.57 (t, J=9.0 Hz, 1H); 4.67 (dd, J=4.0 Hz, J=5.0 Hz, 1H); 4.69 (dd, J=5.0 Hz, J=9.5 Hz, 1H); 4.75 (t, J=8.0 Hz, 1H); 6.17 (dd, J=9.3 Hz, J=15.8 Hz, 1H); 6.55 (d, J=16.0 Hz, 1H); 7.09-7.12 (m, 2H); 7.19-7.42 (m, 13H).

The compound of Example 10A is used to prepare other amide and ester derivatives, such as the amides and esters represented by the group A in compounds of formulae (I), (II), and (III).

Example 11A (S)-(benzyl)-D-cysteine-[4-(2-(1-piperidyl)ethyl)]piperidinenamide,dihydrochloride. N-tButyloxycarbonyl-(S)-(benzyl)-D-cysteine-[4-(2-(1-piperidyl)ethyl)]piperidinenamide (0.453 g, 0.93 mmole) was reacted overnight with acetyl chloride (0.78 mL, 13.80 mmole) in anhydrous methanol (15 mL). The title compound was obtained as an off-white solid by evaporating the reaction mixture to dryness (0.417 g, 97%). $^1$H NMR (CD$_3$OD) δ 0.94-1.29 (m, 2H); 1.49-1.57 (m, 1H); 1.62-1.95 (m, 10H); 2.65-2.80 (m, 2H); 2.81-2.97 (m, 4H); 3.01-3.14 (m, 2H); 3.50-3.60 (m, 3H); 3.81-3.92 (m, 2H); 4.41-4.47 (m, 2H); 7.25-7.44 (m, 5H).

Example 12A tert-Butyl[3(S)-(4(S)-phenyloxazolidin-2-on-3-yl)-4(R)-(2-styryl)azetidin-2-on-1-yl]acetate. The imine prepared from 4.53 g (34.5 mmol) glycine tert-butyl ester and cinnamaldehyde was combined with 2-(4(S)-phenyloxazolidin-2-on-3-yl)acetyl chloride (Example 1A) according to the procedure of Example 9, to give 5.5 g (30%) of Example 15 as colorless crystals (recrystallized, n-chlorobutane); mp 194-195° C.

Example 13

General procedure for alklylation and/or acylation of an (Azetidin-2-on-1-yl)acetate. A solution of (azetidin-2-on-1-yl)acetate in tetrahydrofuran (0.22 M in azetidinone), such as Example 12A, is cooled to −78° C. and is with lithium bis(trimethylsilyl)amide (2.2 equivalents). The resulting anion is treated with an appropriate alkyl or acyl halide (1.1 equivalents). Upon complete conversion of the azetidinone, the reaction is quenched with saturated aqueous ammonium chloride and partitioned between ethyl acetate and water. The organic phase is washed sequentially with 1N hydrochloric acid, saturated aqueous sodium bicarbonate, and saturated aqueous sodium chloride. The resulting organic layer is dried (magnesium sulfate) and evaporated. The residue is purified by silica gel chromatography with an appropriate eluent, such as 3:2 hexane/ethyl acetate.

This procedure is used to prepare compounds of formulae (I), (II), and (III) by an alternate synthetic route from a common intermediate such as tert-Butyl[3(S)-(4(S)-phenyloxazolidin-2-on-3-yl)-4(R)-(2-styryl)azetidin-2-on-1-yl]acetate, and related compounds. This procedure is also used to prepare alkylated and acylated analogs of the compounds described herein, such as compounds of formulae (I), (II), and (III) wherein R$^1$ is other than hydrogen. It is further appreciated that this procedure may be modified to introduce additional groups onto the azetidinone ring to prepare compounds described herein where R$^2$ is other than hydrogen.

It is appreciated that the epimers of these compounds at the carbon alpha to the azetidinone may also be prepared by the procedures described above, by selecting the appropriate starting materials. Further, all other compounds falling within the scope of the compounds of formula (I), (II), and (III) may also be generally prepared by the foregoing examples.

In another embodiment, the compounds described herein are useful for antagonism of the vasopressin $V_{1a}$, $V_{1b}$, and $V_2$ receptors in methods for treating patients suffering from disease states and conditions that are responsive to antagonism of the vasopressin $V_{1a}$, $V_{1b}$, and $V_2$ receptors. Illustratively, the methods described herein include the step of administering to a subject or patient in need of such treatment an effective amount of a compound described by the formulae herein. Antagonism of various vasopressin receptor subtypes has been associated with numerous physiological and therapeutic benefits. These benefits may arise from antagonism of both peripheral and central nervous system vasopressin receptors. Peripheral nervous system utilities include administration of vasopressin $V_{1a}$ and/or vasopressin $V_2$ antagonists as adjuncts in heart failure or as antithrombotic agents. Central nervous system effects include administration of vasopressin $V_{1a}$ and/or vasopressin $V_{1b}$ antagonists of the compounds described herein for the treatment of obsessive-compulsive disorder, aggressive disorders, depression, anxiety, and other psychological and neurological disorders.

Illustrative disease states that are responsive to the antagonism of a vasopressin $V_2$ receptor and treatable by the methods described herein include various cardiovascular diseases, including, disorders or conditions associated with platelet aggregation, and the like. In addition, methods for treating other disease states and conditions treatable by for example oxytocin receptor antagonism, tachykinin receptor antagonism, neurokinin 1 receptor antagonism, neurokinin 2 receptor antagonism, and the like are described herein, where the method includes the step of administering to a patient in need of relief from such a disease state or condition an effective amount of one or more substituted 2-(azetidin-2-on-1-yl)alkanedioic acids, substituted 2-(azetidin-2-on-1-yl)hydroxyalkylalkanoic acids, substituted 2-(azetidin-2-on-1-yl)alkylalkanoic acids, and analogs and derivatives thereof described herein.

Method Example 1

Human vasopression $v_{1b}$ receptor-expressing cells. Human vasopressin receptor 1B (HV1B) cDNA (see, Lolait et al., "Extrapituitary expression of the rat V1b vasopressin receptor gene" Proc. Natl. Acad. Sci. USA. 92:6783-7 (1995); de Keyzer et al., "Cloning and characterization of the human V3(V1b) pituitary vasopressin receptor" FEBS Lett. 356: 215-20 (1994); Sugimoto et al., "Molecular cloning and functional expression of a cDNA encoding the human V1b vasopressin receptor" S. Biol. Chem. 269:27088-92 (1994)) was inserted into a mammalian cell expression vector PCI-neo (Promega) at EcoR1 site. The recombinant plasmid carrying HV1B cDNA was identified from transformed *E. Coli* clones and used for the transfection of Chinese hamster ovary cell (CHO-K1, ATCC). Two micrograms of HV1B receptor DNA was introduced into 10$^5$ CHO cells cultured in 6-well plate, using Fugene-6 mediated transfection technique (Boehringer Mannheim). Twenty-four hrs post transfection, Cells were then cultured under selection of G-418 (0.25 mg/ml) supplemented to the culture medium. Three days later, limited dilution was carried out to obtain single cell clones in 96-well plates. After a period of 2-weeks of growth, monoclones were expanded into two sets of 12-well plates. When confluence was reached, one set of wells were assayed for their ability to bind tritium-labeled arginine-vasopressin (NEN). Nine positive clones were initially identified out of 60 clones screened, and clones that demonstrated highest AVP binding were saved as permanent cell lines for HV1B affinity screening of Serenix compounds.

Method Example 2

Human or Rat Vasopression $V_{1a}$, $V_{1b}$, and/or $V_2$ cell-based receptor binding assay. The $V_{1a}$, $V_{1b}$, and/or $V_2$ cell lines (cells expressing either the human or rat $V_{1a}$, $V_{1b}$, and/or $V_2$ receptors) were grown in alpha-MEM medium supplemented with 10% fetal bovine serum and 250 ug/ml G418 (Gibco, Grand Island, N.Y.) in 75 cm² flask. For competitive binding assay, hV1b cells were dissociated with enzyme-free, PBS based cell dissociation solution (Specialty Media, Phillipursburg, N.J.), following the manufacturer's protocol. Cells were plated into 12-well culture plates at a rate of one flask to 18 plates (rate should be adjusted according to the extent of confluency), and maintained in culture for 2-3 days. Culture medium was then removed, cells were washed once with 2 ml binding buffer (25 mM Hepes, 0.25% BSA, 1×DMEM, PH=7.0) at room temperature. To each well, 990 ul binding buffer containing 1 nM ³H-AVP was added, and followed by the addition of 10 ul series diluted testing compounds or cold AVP, all dissolved in DMSO. All incubations were in triplicate, and dose-inhibition curves consisted of total binding (DMSO only) and 5 concentrations (0.1, 1.0, 10, 100, and 1000 nm) of test agent, or cold AVP, encompassing the IC50. Cells were incubated for 30 min at 37° C. in a moisturized incubator. Assay mixture was then removed and each well was washed three times with PBS (pH=7.4). After washing, 1 ml 2% SDS was added per well and plates were let sit for 15 min at RT. Gently pat the plate to make sure that lysed cells were detached. The whole content in a well was transferred to a scintillation vial. Each well was then rinsed with 0.5 ml PBS and added to the corresponding vial. Scintillation fluid (Ecoscint, National Diagnostics, Atlanta, Ga.) was then added at 3 ml per vial. Samples were counted in a liquid scintillation counter (Beckman LS3801). IC50 and Ki values were calculated using Prism Curve fitting software.

Selected examples were tested in these assay on cells expressing human $V_{1a}$ or human $V_{1b}$ receptors. Binding affinities (IC$_{50}$) for illustrative compounds are summarized in the following Table. Inhibition constants (K$_i$) for illustrative compounds are also summarized in the following Table.

| Example | Human $V_{1a}$ Binding Affinity (IC$_{50}$ (nM)) | Human $V_{1a}$ Binding Affinity (K$_i$ (nM)) | Human $V_{1b}$ Binding Affinity (IC$_{50}$ (μM)) | Human $V_{1b}$ Binding Affinity (K$_i$ (μM)) |
|---|---|---|---|---|
| 9B | 0.11 | 0.07 | 1.10 | 0.69 |

Method Example 3

Inhibition of Vasopressin $V_{1b}$-Mediated Phosphatidylinositol Turnover, a functional assay for antagonist activity. The physiological effects of vasopressin are mediated through specific G-protein coupled receptors. The vasopressin $V_{1a}$, $V_{1b}$, and/or $V_2$ receptors are coupled to a G protein, which is coupled to cAMP. The agonist or antagonist character of the compounds described herein may be determined by their ability to inhibit vasopressin-mediated turnover of phosphatidylinositol by using conventional methods, including the procedure described in the following paragraphs.

Cells expressing the human or rat $V_{1a}$, $V_{1b}$, and/or $V_2$ receptors are grown in alpha-modified minimal essential medium containing 10% fetal bovine serum and 0.25 mg/ml G418. Three days prior to the assay, near-confluent cultures are dissociated and seeded in 6-well tissue culture plates, about 100 wells being seeded from each 75 cm² flask (equivalent to 12:1 split ratio). Each well contains 1 ml of growth medium with 2 μCi of [³H] myo-inositol (American Radiolabeled Chemicals, St. Louis, Mo.).

All assays are in triplicate except for basal and 10 nM AVP (both n=6). Arginine vasopressin (AVP) is dissolved in 0.1N acetic acid. Candidate drugs are dissolved in DMSO on the day of the experiment and diluted in DMSO to 200 times the final test concentration. Candidate drugs and AVP (or corresponding volumes of DMSO) are added separately as 5 ul in DMSO to 12×75 mm glass tubes containing 1 ml of assay buffer (Tyrode's balanced salt solution containing 50 mM glucose, 10 mM LiCl, 15 mM HEPES pH 7.4, 10 uM phosphoramidon, and 100 uM bacitracin). The order of incubations are randomized. Incubations are initiated by removing the prelabeling medium, washing the monolayer once with 1 ml of 0.9% NaCl, and adding the contents of the assay tubes. The plates are incubated for 1 hr at 37° C. Incubations are terminated by removing the incubation medium and adding 500 ul of ice cold 5% (w/v) trichloroacetic acid and allowing them to stand for 15 min.

The incubates are fractionated on BioRad Poly-Prep Econo-Columns packed with 0.3 ml of AG 1 X-8100-200 formate resin. Resin is mixed 1:1 with water and 0.6 ml added to each column. Columns are then washed with 10 ml water. Scintillation vials (20 ml) are placed under each column. For each incubation well, the contents are transferred to a minicolumn, after which the well is washed with 0.5 ml distilled water, which is also added to the minicolumn. The columns are then washed twice with 5 ml of 5 mM myo-inositol to elute free inositol. A 1 ml aliquot of this is transferred to a new 20 ml scintillation vial, plus 10 ml of Beckman Ready Protein Plus, and counted. After the myo-inositol wash is complete, empty scintillation vials are placed under the columns, and [³H] inositol phosphates are eluted with three additions of 1 ml 0.5 M ammonium formate containing 0.1 N formic acid. Elution conditions are optimized to recover inositol mono-, bis-, and trisphosphates, without eluting the more metabolically inert tetrakis-, pentakis-, and hexakis-phosphates. Samples are counted in a Beckman LS 6500 multipurpose scintillation counter after addition of 10 ml Tru-Count High Salt Capacity scintillation fluid.

Inositol lipids are measured by adding 1 ml of 2% sodium dodecyl sulfate (SDS) to each well, allowing the wells to sit for at least 30 min. Lysed content in each well is transferred to a 20 ml scintillation vial. 10 ml Beckman Ready Protein Plus scintillation fluid is added and radioactivity counted.

Concentration-response curves for AVP and concentration-inhibition curves for test agents versus 10 nM AVP were analyzed by nonlinear least-squares curve-fitting to a 4-parameter logistic function. Parameters for basal and maximal inositol phosphates, EC$_{50}$- or IC$_{50}$, and Hill coefficient were varied to achieve the best fit. The curve-fitting was weighted under the assumption that the standard deviation was proportional to dpm of radioactivity. Full concentration-response curves for AVP were run in each experiment, and $IC_{50}$ values were converted to $K_i$ values by application of the Cheng-Prusoff equation, based on the $EC_{50}$ for AVP in the same experiment. Inositol phosphates were expressed as dpm per $10^6$ dpm of total inositol incorporation.

Experiments to test for competitively of test agents consisted of concentration-response curves for AVP in the absence and presence of two or more concentrations of test agent. Data were fit to the following competitive logistic equation:

$$Y = B + \frac{M \times \{A/[E+(D/K)]\}^Q}{1+\{A/[E+(D/K)]\}^Q}$$

where Y is dpm of inositol phosphates, B is concentration of basal inositol phosphates, M is the maximal increase in concentration of inositol phosphates, A is the concentration of agonist (AVP), E is the $EC_{50}$ for agonist, D is the concentration of the antagonist, K is the $K_i$ for antagonist, and Q is the cooperativity (Hill coefficient).

Experiments to test for competition by test agents consist of concentration-response curves for AVP in the absence and presence of at least five concentrations of test agent. Ki values, which reflect the antagonistic activities against AVP in the production of signaling molecule IP3, are calculated with prism software based on Cheng and Prusoff equation.

Method Example 4

Seed finding by golden hamsters. It is appreciated that a hamster's ability to find seeds under certain conditions may reflect their level of anxiety. This method for assaying seed finding capabilities in hampsters treated with the compounds described herein is an animal model of anxiety.

Male, Syrian golden hamsters (*Mesocricetus auratus*) (120-130 g) obtained from Harlan Sprague-Dawley Laboratories (Indianapolis, Ind.) are housed individually in Plexiglas cages (24 cm×24 cm×20 cm), maintained on a reverse light:dark cycle (14:10; lights on at 19:00 hr), and provided food and water ad libitum. All tests are conducted during the dark phase of the circadian cycle under dim red illumination. Prior to testing, all animals are fasted for 20-24 hrs. Ninety min after intraperitoneal (IP) injection of SRX262 (n=10) or saline vehicle (n=10), animals are taken from their home cage and placed into a holding cage for 2 min. During their absence, six sunflower seeds were buried under the bedding in one corner of their home cage. Animals are placed back into their home cage randomly facing any one of the empty corners and timed for their latency to find the seeds during a five minute observation period. The latency to find the seeds is reduced following treatment with the compounds described herein and comparable in magnitude to fluoxetine, buspirone, and chlordiazapoxide.

Method Example 5

Social subjugation in hamsters, a biochemical marker assay. There is a body of literature on the neuroendocrine and behavioral consequences of repeated social subjugation in adult male golden hamsters. In adult animals, losing fights and being relegated to low social status is very stressful, resulting in altered levels of adrenal and gonadal steroids together with changes in social behaviors (Rose et al., 1975; Eberhart et al., 1980, 1983). Studies on adult male hamsters show depressed levels of testosterone and elevated levels of glucocorticoids following repeated defeat by dominant conspecifics (Huhman et al., 1991).

Male hamsters are housed and maintained as described above. For 30 minutes each day for fourteen consecutive days, animals are exposed to threat and attack from a larger conspecific (n=14). Following these daily episodes of traumatic stress animals are left undisturbed in their home cages for ten days. During this recovery period animals are treated with the compounds described herein (1 mg/kg/day) (n=7) or saline vehicle (n=7). At the end of this treatment period animals are sacrificed by decapitation and trunk blood collected for the radioimmunoassay of testosterone and cortisol. The testosterone levels of chronically subjugated hamsters are very low while the basal cortisol levels are high. This neuroendocrine profile is altered by treatment with the compounds described herein. The collected data indicate that blocking $V_{1b}$ receptors can enhance recovery from traumatic stress like social subjugation.

Method Example 6

Social subjugation in hamsters, a behavioral assay, screening for antidepression-like activity. The hamster model of social subjugation in the resident intruder paradigm is used. The resident/intruder model of aggression relies on the motivation of a resident animal to chase and fight intruders coming into their territory (Miczek 1974). Smaller animals placed into the home cage of a resident will be more easily defeated and become socially subjugated with repeated encounters. Social subjugation is a significant and natural stressor in the animal kingdom. Animals defeated and subjugated during establishment of dominance hierarchies or territorial encounters can be highly submissive in future agonistic interactions.

For example, defeated mice display less aggression and more submissive behavior (Frishknecht et al., 1982; Williams and Lierle 1988). Rats consistently defeated by more aggressive conspecifics show a behavioral inhibition characterized by less social initiative and offensive aggression, as well as an increase in defensive behavior (Van de Poll et al., 1982). Repeatedly defeated male hamsters respond in a submissive manner when confronted by a non-aggressive intruder (Potegal et al., 1993), in addition their normal reproductive behavior is reduced as measured by latency to mount a receptive female. Moreover, following repeated defeat by a dominant conspecific, a resident hamster will be defensive or fearful of smaller-sized non aggressive intruders (Potegal et al., 1993). The generalization of submissive behavior toward non-threatening, novel stimulus animals is an example of "conditioned defeat" (Potegal et al., 1993). Conditioned defeat in adult hamsters is not permanent as the flight and defensive behaviors disappear over many weeks. Animals displaying conditioned defeat are treated with the compounds described herein, and observed for a return to normal aggressive and reproductive behaviors.

In addition, social subjugation has a pronounced effect on the animal's neuroendocrinology. In adult animals, losing fights and being relegated to low social status alters levels of adrenal and gonadal steroids (Rose et al., 1975; Eberhart et al., 1908, 1983). Adult male hamsters show depressed levels of testosterone and elevated levels of glucocorticoids following repeated defeat by dominant conspecifics (Huhman et al., 1991). Recovery of normal testosterone and cortisol levels is assessed in animals treated with the compounds described herein.

Male, Syrian golden hamsters (*Mesocricetus auratus*) (120-130 g) obtained from Harlan Sprague-Dawley Laboratories (Indianapolis, Ind.) are housed individually in Plexiglas cages (24 cm×24 cm×20 cm), maintained on a reverse light:dark cycle (14:10; lights on at 19:00 hr), and provided food and water ad libitum. All tests are conducted during the dark phase of the circadian cycle under dim red illumination. Each compound is tested in 3 doses (100 μg, 1 mg, and 10 mg/kg) plus saline vehicle. Twenty-four animals (six per group) are tested. Animals are socially subjugated by placing them into the home cage of a larger hamster each day for 30 min for 14 consecutive days. Animals are exposed to a different resident each day so that the threat and attack is unremitting. Following the cessation of social subjugation, animals are allowed to recover undisturbed in their home cage for the next two weeks. During this time they are treated with a compound described herein, or with vehicle for one week. At the end of the week, the animals are tested for aggression toward a smaller intruder placed into their home cage. Animals are scored for latency to bite, number of bites, and contract time. On the following day, a receptive female is placed into the animals home cage, and the animal is scored for latency to mount. At the end of two weeks, animals are sacrificed and trunk blood assayed for testosterone and cortisol. All animals are sacrificed during the first 2 hrs of the dark phase of the light:dark cycle to minimize circadian variations in cortisol levels. The data between treatments is compared with one-way, ANOVA followed by Bonferroni post hoc tests.

Method Example 7

Elevated plus maze. The elevated plus-maze was developed for screening anxiolytic and anxiogenic drug effects in rodents. The method has been validated behaviorally, physiologically, and pharmacologically. The plus-maze consists of two open arms and two enclosed arms. Rats and mice tend to naturally make fewer entries into the open arms than into the closed arms and will spend significantly less time in open arms. Confinement to the open arms is associated with significantly more anxiety-related behavior and higher stress hormone levels than confinement to the closed arms. Clinically effective anxiolytics, e.g., chlordiazepoxide or diazepam, significantly increase the percentage of time spent in the open arms and the number of entries into the open arms. Conversely, anxiogenic compounds like yohimbin or amphetamines reduce open arm entries and time spent in the open arms.

Male mice are group housed in a normal 12:12 light:dark cycle with light on at 0800 hr and provided food and water ad libitum. The plus-maze consists of two open arms, 40 cm long, 6 cm wide with no walls. The two closed arms have the same dimensions with walls 25 cm high. Each pair of arms are arranged opposite to each other to form the plus-maze. The maze is elevated to a height of 50 cm. Each drug is tested in 3 doses (100 μg, 1 mg, and 10 mg/kg) plus saline vehicle. Twenty-four animals (six per group) are tested in the plus-maze 90 min following the IP injection in a volume of ca. 0.1 ml. At the start of the experiment, the animal is placed at the end of one of the open arms. Over a five min observation period, animals are scored for the latency to enter the closed arm, time spent in the closed arm, and the number of open arm entries following the first occupation of the closed arm. The data between treatments are compared with one-way, ANOVA followed by Bonferroni post hoc tests.

Method Example 8

Impulsivity/inappropriate aggression. Impulsivity and/or inappropriate aggression may be determined using standard animal behavior assays, including the resident-intruder paradigm, the isolation induced aggression paradigm, and the interfemale aggression and/or intermale aggression paradigms. These assays may be applied to mice, rats, and/or hamsters. Arginine vasopressin (AVP) has been implicated in the aggressive behaviors of a number of species, including humans (see, Coccaro et al., "Cerebrospinal fluid vasopressin levels: correlates with aggression and serotonin function in personality-disordered subjects" Arch. Gen. Psychiatry 55:708-14 (1998)). Infusions of AVP receptors antagonists have been shown to reduce aggression (see, Ferris & Potengal, "Vasopressin receptor blockade in the anterior hypothalamus suppresses aggression in hamsters" Physiol. Behav. 44:235-39 (1988)). A study of the vasopressin $V_{1b}$ knockout mouse indicated reductions in aggressive behavior by these animals (see, Wersinger et al., "Vasopressin $V_{1b}$ receptor knockout reduces aggressive behavior in male mice" Mol. Psychiatry. 7:975-84 (2002)).

Adult male Syrian hamsters (*Mesocricetus auratus*, Charles River Laboratories) are used as subjects. Hamsters to be used as residents are housed individually for at least 2 weeks prior to the beginning of the experiment. A subpopulation of smaller males are used as intruders, which are group-housed (three/cage) in order to minimize aggression levels. Resident and intruder pairs should have a minimum of about a 10-g weight difference. For example, the weight range for residents is between 105 and 150 g, and intruder weights ranged from 95 to 140 g, although these absolute weights may vary. Animals are housed in Plexiglas cages (46.0×24.0×21.0 cm) with corn cob bedding in a temperature (e.g. 69° F.) and humidity-controlled room with food and water available ad libitum, which is maintained on a 14:10 light-dark cycle with lights off at 12:00 noon. Tests are run under red light illumination during the first 3 h of the dark phase of the light-dark cycle. All animals are handled daily for 10 days prior to the start of the study.

A single nondrug screening test (resident-intruder) is run with each individually housed hamster to determine the baseline levels of aggression of the animal. Only resident males that show a minimum of one bite during the test session are used in the drug test. Tests with the compounds described herein are run 48 h after the screening test. Twenty-five minutes after drug administration, residents are moved to the testing room. Intruders are introduced into the resident home cage 5 min later, for a 10-min test. Each resident is confronted with a different intruder than was used in the screening phase. It is to be understood that the protocols used in this experiment are in compliance with the applicable state and federal regulations. Behavioral measures include attack latency, latency to bite, and number of bites. Data are analyzed by one-way ANOVA, optionally followed by Newman-Keuls post hoc tests. Further details of this assay are found in Blanchard et al., "AVP V1b selective antagonist SSR149415 blocks aggressive behaviors in hamsters" Pharmacol., Biochem. Behav. 80:189-94 (2005).

Method Example 9

Human oxytocin binding and functional assay. Oxytocin is known for its hormonal role in parturition and lactation. Oxytocin agonists are useful clinically to induce lactation; induce or augment labor; control postpartum uterine atony and hemmorhage; cause uterine contraction after cesarean section or during other uterine surgery; and to induce therapeutic abortion. Oxytocin, acting as a neurotransmitter in the central nervous system, also plays an important role in the expression of central functions such as maternal behavior, sexual behavior (including penile erection, lordosis and copulatory behavior), yawning, tolerance and dependance mechanisms, feeding, grooming, cardiovascular regulation and thermoregulation (Argiolas and Gessa, *Neuroscience and Biobehavioral Reviews*, 15:217-231 (1991)). Oxytocin antagonists find therapeutic utility as agents for the delay or prevention of premature labor; or to slow or arrest delivery for brief periods in order to undertake other therapeutic measures.

Compounds described herein are also believed to be oxytocin agents. Oxytocin preparations and a number of oxytocin agonists are commercially available for therapeutic use. In recent years, oxytocin antagonists with antiuterotonic activity have been developed and evaluated for their potential use in the treatment of preterm labor and dysmenorrhyea (Pavo et al., *J. Med. Chem.*, 37:255-259 (1994); Akerlund et al., *Br. J. Obstet. Gynaecol.*, 94:1040-1044 (1987); Akerlund et al., *Br. J. Obstet. Gynaecol.*, 86:484-487 (1979)). The oxytocin antagonist atosiban has been studied clinically and resulted in a more significant inhibition of preterm contractions than did placebo (Goodwin et al., *Am. J. Obstet. Gynecol.*, 170:474 (1994)).

The human oxytocin receptor has been cloned and expressed (Kimura et al., *Nature*, 356:526-529 (1992)), it is identified under the accession number X64878. To demonstrate the affinity of the compounds described herein for the human oxytocin receptor, binding studies were performed using a cell line expressing the human oxytocin receptor in 293 cells (henceforth referred to as the OTR cell line) substantially by the procedure described by Morel et al. (*Nature*, 356:523-526 (1992)). The 293 cell line is a permanent line of primary human embryonal kidney cells transformed by sheared human adenovirus type 5 DNA. It is identified as ATCC CRL-1533.

The OTR cell line was grown in DMEM (Delbecco's Modified Essential Medium, Sigma, St. Louis, Mo., USA) with 10% fetal bovine serum, 2 mM L-glutamine, 200 μg hygromycin (Sigma, St. Louis, Mo., USA) and 250 μg/ml G418 (Gibco, Grand Island, N.Y., USA). To prepare membranes, OTR cells were grown to confluency in 20 roller bottles. Cells were dissociated with enzyme-free cell dissociation medium (Specialty Media, Lavallette, N.J., USA) and centrifuged at 3200 rpm for 15 minutes. The pellet was resuspended in 40 mL of Tris-HCl (tris[hydroxymethyl]aminomethane hydrochloride) buffer (50 mM, pH 7.4) and homogenized for 1 minute with a Tekmar Tissumizer (Cincinnati, Ohio USA). The suspension was centrifuged at 40,000×g for 10 minutes. The pellet was resuspended and centrifuged as above. The final pellet was suspended in 80 mL of Tris 7.4 buffer and stored in 4 mL aliquots at −80° C. For assay, aliquots were resuspended in assay buffer and diluted to 375 μg protein per mL. Protein concentration was determined by BCA assay (Pierce, Rockford, Ill., USA).

Assay buffer was 50 mM Tris-HCl(tris[hydroxymethyl]aminomethane hydrochloride), 5 mM $MgCl_2$, and 0.1% bovine serum albumin at pH 7.4. The radioligand for binding assays was [$^3$H]oxytocin ([tyrosyl-2,6-$^3$H]oxytocin, 48.5 Ci/mmol, DuPont NEN, Boston, Mass., USA). The order of additions was 195 μL assay buffer, 200 μL OTR membranes (75 μg protein) in assay buffer, 5 μL of test agent in dimethylsulfoxide (DMSO) or DMSO alone, and 100 μL [$^3$H]oxytocin in assay buffer (final concentration 1.0 nM). Incubations were for one hour at room temperature. Bound radioligand was separated from free by filtration on a Brandel cell harvester (Gaithersburg, Md., USA) through Whatman GF/B glass-fiber filters that had been soaked for 2 hours in 0.3% polyethylenimine. The filters were washed with ice-cold 50 mM Tris-HCl (pH 7.7 at 25° C.) and the filter circles were placed in scintillation vials, to which were then added 5 mL Ready Protein Plus™ scintillation fluid, and counted in a liquid scintillation counter. All incubations were in triplicate, and dose-inhibition curves consisted of total binding, nonspecific binding (100 μM oxytocin, Sigma, St. Louis, Mo., USA), and 6 or 7 concentrations of test agent encompassing the $IC_{50}$. Total binding was typically about 1,000 cpm and nonspecific binding about 200 cpm. $IC_{50}$ values were calculated by non-linear least-squares curve-fitting to a 4-parameter logistic model. Certain compounds of formula (I) have shown affinity for the oxytocin receptor.

Several bioassays are available to determine the agonist or antagonist character of compounds exhibiting affinity at the oxytocin receptor. One such assay is described in U.S. Pat. No. 5,373,089, hereby incorporated by reference. Said bioassay is derived from procedures described in a paper by Sawyer et al. (*Endocrinology*, 106:81 (1980)), which in turn was based on a report of Holton (*Brit. J. Pharmacol.*, 3:328 (1948)). The assay calculations for $pA_2$ estimates are described by Schild (*Brit. J. Pharmacol.*, 2:189 (1947)).

Method Example 10

Assay for oxytocin functional activity.

1. Animals: a 1.5 cm piece of uterus from a virgin rat (Holtzman) in natural estrus is used for the assay.

2. Buffer/Assay Bath: The buffer used is Munsicks. This buffer contains 0.5 mM $Mg^{2+}$. The buffer is gassed continuously with 95% oxygen/5% carbon dioxide giving a pH of 7.4. The temperature of the assay bath is 37° C. A 10 mL assay bath is used that contains a water jacket for maintaining the temperature and inlet and outlet spikets for adding and removing buffer.

3. Polygraph/transducer: The piece of uterine tissue used for the assay is anchored at one end and connected to a Statham Strain Gauge Force Transducer at the other end which in turn is attached to a Grass Polygraph Model 79 for monitoring the contractions.

4. Assay Protocol:

(a) The tissue is equilibrated in the assay bath for one hour with washing with new buffer every 15 minutes. One gram of tension is kept on the tissue at all times.

(b) The tissue is stimulated initially with oxytocin at 10 nM to acclimate the tissue and with 4 mM potassium chloride (KCl) to determine the maximum contractile response.

(c) A cumulative dose response curve is then done with oxytocin and a concentration of oxytocin equivalent to approximately 80% of the maximum is used for estimating the $pA_2$ of the antagonist.

(d) The tissue is exposed to oxytocin (Calbiochemical, San Diego, Calif.) for one minute and washed out. There is a three minute interval before addition of the next dose of agonist or antagonist. When the antagonist is tested, it is given five minutes before the agonist. The agonist is given for one minute. All responses are integrated using a 7P10 Grass Integrator. A single concentration of oxytocin, equal to 80% of the maximum response, is used to test the antagonist. Three different concentrations of antagonists are used, two that will reduce the response to the agonist by less than 50% and one that will reduce the response greater than 50% (ideally this relation would be 25%, 50% and 75%). This is repeated three times for each dose of antagonist for a three point assay.

(e) Calculations for $pA_2$—The dose-response (DR) ratios are calculated for antagonist and a Schild's Plot is performed by plotting the Log (DR-1) vs. Log of antagonist concentration. The line plotted is calculated by least-squares regression analysis. The $pA_2$ is the concentration of antagonist at the point where the regression line crosses the 0 point of the Log (DR-1) ordinate. The $pA_2$ is the negative Log of the concentration of antagonist that will reduce the response to the agonist by one-half.

Method Example 11

Tachykinin receptor binding assay. Compounds described herein are believed to be tachykinin agents. Tachykinins are a family of peptides which share a common amidated carboxy terminal sequence. Substance P was the first peptide of this family to be isolated, although its purification and the determination of its primary sequence did not occur until the early 1970's. Between 1983 and 1984 several groups reported the isolation of two novel mammalian tachykinins, now termed neurokinin A (also known as substance K, neuromedin 1, and neurokinin α), and neurokinin B (also known as neuromedin K and neurokinin β). See, J. E. Maggio, *Peptides*, 6 (Supplement 3): 237-243 (1985) for a review of these discoveries.

Tachykinin receptor antagonists are of value in the treatment of a wide variety of clinical conditions which are characterized by the presence of an excess of tachykinin. These clinical conditions may include disorders of the central nervous system such as anxiety, depression, psychosis, and schizophrenia; neurodegenerative disorders such as dementia, including senile dementia of the Alzheimer's type, Alzheimer's disease, AIDS-associated dementia, and Down's syndrome; demyelinating diseases such as multiple sclerosis and amyotrophic lateral sclerosis and other neuropathological disorders such as peripheral neuropathy, such as diabetic and chemotherapy-induced neuropathy, and post-herpetic and other neuralgias; acute and chronic obstructive airway diseases such as adult respiratory distress syndrome, bronchopneumonia, bronchospasm, chronic bronchitis, drivercough, and asthma; inflammatory diseases such as inflammatory bowel disease, psoriasis, fibrositis, osteoarthritis, and rheumatoid arthritis; disorders of the musculo-skeletal system, such as osteoporosis; allergies such as eczema and rhinitis; hypersensitivity disorders such as poison ivy; ophthalmic diseases such as conjunctivitis, vernal conjunctivitis, and the like; cutaneous diseases such as contact dermatitis, atopic dermatitis, urticaria, and other eczematoid dennatites; addiction disorders such as alcoholism; stress-related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal disorders or diseases associated with the neuronal control of viscera such as ulcerative colitis, Crohn's disease, emesis, and irritable bowel syndrome; disorders of bladder function such as bladder detrusor hyper-reflexia and incontinence; artherosclerosis; fibrosing and collagen diseases such as scleroderma and eosinophilic fascioliasis; irritative symptoms of benign prostatic hypertrophy; disorders of blood flow caused by vasodilation and vasospastic diseases such as angina, migraine, and Raynaud's disease; and pain or nociception, for example, that attributable to or associated with any of the foregoing conditions, especially the transmission of pain in migraine.

Tachykinins are widely distributed in both the central and peripheral nervous systems. When released from nerves, they exert a variety of biological actions, which, in most cases, depend upon activation of specific receptors expressed on the membrane of target cells. Tachykinins are also produced by a number of non-neural tissues. The mammalian tachykinins substance P, neurokinin A, and neurokinin B act through three major receptor subtypes, denoted as NK-1, NK-2, and NK-3, respectively. These receptors are present in a variety of organs.

Substance P is believed inter alia to be involved in the neurotransmission of pain sensations, including the pain associated with migraine headaches and with arthritis. These peptides have also been implicated in gastrointestinal disorders and diseases of the gastrointestinal tract such as inflammatory bowel disease. Tachykinins have also been implicated as playing a role in numerous other maladies, as discussed infra.

In view of the wide number of clinical maladies associated with an excess of tachykinins, the development of tachykinin receptor antagonists will serve to control these clinical conditions. The earliest tachykinin receptor antagonists were peptide derivatives. These antagonists proved to be of limited pharmaceutical utility because of their metabolic instability. Recent publications have described novel classes of non-peptidyl tachykinin receptor antagonists which generally have greater oral bioavailability and metabolic stability than the earlier classes of tachykinin receptor antagonists. Examples of such newer non-peptidyl tachykinin receptor antagonists are found in European Patent Publication 591,040 A1, published Apr. 6, 1994; Patent Cooperation Treaty publication WO 94/01402, published Jan. 20, 1994; Patent Cooperation Treaty publication WO 94/04494, published Mar. 3, 1994; Patent Cooperation Treaty publication WO 93/011609, published Jan. 21, 1993, Patent Cooperation Treaty publication WO 94/26735, published Nov. 24, 1994. Assays useful for evaluating tachykinin receptor antagonists are well known in the art. See, e.g., J. Jukic et al., *Life Sciences*, 49:1463-1469 (1991); N. Kucharczyk et al., *Journal of Medicinal Chemistry*, 36:1654-1661 (1993); N. Rouissi et al., *Biochemical and Biophysical Research Communications*, 176:894-901 (1991).

Method Example 12

NK-1 Receptor Binding Assay. NK-1 antagonists are useful in the treatment of pain, especially chronic pain, such as neuropathic pain, post-operative pain, and migraines, pain associated with arthritis, cancer-associated pain, chronic lower back pain, cluster headaches, herpes neuralgia, phantom limb pain, central pain, dental pain, neuropathic pain, opioid-resistant pain, visceral pain, surgical pain, bone injury pain, pain during labor and delivery, pain resulting from burns, including sunburn, post partum pain, angina pain, and genitourinary tract-related pain including cystitis.

In addition to pain, NK-1 antagonists are especially useful in the treatment and prevention of urinary incontinence; irritative symptoms of benign prostatic hypertrophy; motility disorders of the gastrointestinal tract, such as irritable bowel syndrome; acute and chronic obstructive airway diseases, such as bronchospasm, bronchopneumonia, asthma, and adult respiratory distress syndrome; artherosclerosis; inflammatory conditions, such as inflammatory bowel disease, ulcerative colitis, Crohn's disease, rheumatoid arthritis, osteoarthritis, neurogenic inflammation, allergies, rhinitis, cough, dermatitis, urticaria, psoriasis, conjunctivitis, emesis, irritation-induced miosis; tissue transplant rejection; plasma extravasation resulting from cytokine chemotherapy and the like; spinal cord trauma; stroke; cerebral stroke (ischemia); Alzheimer's disease; Parkinson's disease; multiple sclerosis; amyotrophic lateral sclerosis; schizophrenia; anxiety; and depression.

Radioreceptor binding assays were performed using a derivative of a previously published protocol. D. G. Payan et al., *Journal of Immunology*, 133:3260-3265 (1984). In this assay an aliquot of IM9 cells ($1 \times 10^6$ cells/tube in RPMI 1604 medium supplemented with 10% fetal calf serum) was incubated with 20 pM $^{125}$I-labeled substance P in the presence of increasing competitor concentrations for 45 minutes at 4° C.

The IM9 cell line is a well-characterized cell line which is readily available to the public. See, e.g., *Annals of the New York Academy of Science*, 190:221-234 (1972); *Nature (London)*, 251:443-444 (1974); *Proceedings of the National Academy of Sciences (USA)*, 71:84-88 (1974). These cells were routinely cultured in RPMI 1640 supplemented with 50 µg/mL gentamicin sulfate and 10% fetal calf serum.

The reaction was terminated by filtration through a glass fiber filter harvesting system using filters previously soaked for 20 minutes in 0.1% polyethylenimine. Specific binding of labeled substance P was determined in the presence of 20 nM unlabeled ligand.

Method Example 13

NK-2 receptor binding assay. NK-2 antagonists are useful in the treatment of urinary incontinence, bronchospasm, asthma, adult respiratory distress syndrome, motility disorders of the gastrointestinal tract, such as irritable bowel syndrome, and pain.

The CHO-hNK-2R cells, a CHO-derived cell line transformed with the human NK-2 receptor, expressing about 400,000 such receptors per cell, were grown in 75 cm$^2$ flasks or roller bottles in minimal essential medium (alpha modification) with 10% fetal bovine serum. The gene sequence of the human NK-2 receptor is given in N. P. Gerard et al., *Journal of Biological Chemistry*, 265:20455-20462 (1990).

For preparation of membranes, 30 confluent roller bottle cultures were dissociated by washing each roller bottle with 10 ml of Dulbecco's phosphate buffered saline (PBS) without calcium and magnesium, followed by addition of 10 ml of enzyme-free cell dissociation solution (PBS-based, from Specialty Media, Inc.). After an additional 15 minutes, the dissociated cells were pooled and centrifuged at 1,000 RPM for 10 minutes in a clinical centrifuge. Membranes were prepared by homogenization of the cell pellets in 300 mL 50 mM Tris buffer, pH 7.4 with a TEKMAR® homogenizer for 10-15 seconds, followed by centrifugation at 12,000 RPM (20,000×g) for 30 minutes using a BECKMAN JA-14® rotor. The pellets were washed once using the above procedure. and the final pellets were resuspended in 100-120 mL 50 mM Tris buffer, pH 7.4, and 4 ml aliquots stored frozen at −70° C. The protein concentration of this preparation was 2 mg/mL.

For the receptor binding assay, one 4-mL aliquot of the CHO-hNK-2R membrane preparation was suspended in 40 mL of assay buffer containing 50 mM Tris, pH 7.4, 3 mM manganese chloride, 0.02% bovine serum albumin (BSA) and 4 µg/mL chymostatin. A 200 µL volume of the homogenate (40 µg protein) was used per sample. The radioactive ligand was [$^{125}$I]iodohistidyl-neurokinin A (New England Nuclear, NEX-252), 2200 Ci/mmol. The ligand was prepared in assay buffer at 20 nCi per 100 µL; the final concentration in the assay was 20 pM. Non-specific binding was determined using 1 µM eledoisin. Ten concentrations of eledoisin from 0.1 to 1000 nM were used for a standard concentration-response curve.

All samples and standards were added to the incubation in 10 µL dimethylsulfoxide (DMSO) for screening (single dose) or in 5 µL DMSO for IC$_{50}$ determinations. The order of additions for incubation was 190 or 195 µL, assay buffer, 200µ: homogenate, 10 or 5 µL sample in DMSO, 100 µL radioactive ligand. The samples were incubated 1 hr at room temperature and then filtered on a cell harvester through filters which had been presoaked for two hours in 50 mM Tris buffer, pH 7.7, containing 0.5% BSA. The filter was washed 3 times with approximately 3 mL of cold 50 mM Tris buffer, pH 7.7. The filter circles were then punched into 12×75 mm polystyrene tubes and counted in a gamma counter.

Method Example 14

Treatment of emesis. In addition to the above indications the compounds described herein may be useful in the treatment of emesis, including acute, delayed, or anticipatory emesis, such as emesis induced by chemotherapy, radiation, toxins, pregnancy, vestibular disorders, motion, surgery, migraine, and variations in intercranial pressure. In particular, the compounds of the formulae described herein may be of use in the treatment of emesis induced by antineoplastic (cytotoxic) agents including those routinely used in cancer chemotherapy.

Examples of such chemotherapeutic agents include alkylating agents, for example, nitrogen mustards, ethyleneimine compounds, alkyl sulfonates, and other compounds with an alkylating action, such as nitrosoureas, cisplatin, and dacarbazine; antimetabolites, for example, folic acid, purine, or pyrimidine antagonists; mitotic inhibitors, for example vinca alkaloids and derivatives of podophyllotoxin; and cytotoxic antibiotics.

Particular examples of chemotherapeutic agents are described, for instance, by D. J. Stewart in NAUSEA AND VOMITING: RECENT RESEARCH AND CLINICAL ADVANCES, (J. Kucharczyk et al., eds., 1991), at pages 177-203. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin, daunorubicin, procarbazine, mitomycin, cytarabine, etoposide, methotrexate, 5-fluorouracil, vinblastine, vincristine, bleomycin, and chlorambucil. R. J. Gralla et al., *Cancer Treatment Reports*, 68:163-172 (1984).

The compounds of the formulae described herein may also be of use in the treatment of emesis induced by radiation, including radiation therapy such as in the treatment of cancer, or radiation sickness; and in the treatment of post-operative nausea and vomiting.

Method Example 15

Inhibition of Platelet Aggregation. Vasopressin $V_2$ receptors are also known to mediate platelet aggregation. Vasopressin receptor agonists cause platelet aggregation, while vasopressin $V_2$ receptor antagonists inhibit the platelet aggregation precipitated by vasopressin or vasopressin agonists. The degree of antagonist activity of the compounds described herein may be determined by using conventional methods, including the assay described in the following paragraphs.

Blood from healthy, human volunteers was collected by venipuncture and mixed with heparin (60 mL of blood added to 0.4 mL of heparinized saline solution (4 mg heparin/mL saline)). Platelet-rich plasma (PRP) was prepared by centrifuging whole blood (150×g), and indomethacin (3 µM) was added to PRP to block the thromboxane-mediated release reaction. PRP was continuously stirred at 37° C. and change in optical density was followed after the addition of arginine vasopressin (AVP) (30 nM) to initiate aggregation. Compounds were dissolved in 50% dimethylsulfoxide (DMSO) and added (10 µL/415 µL PRP) before the addition of AVP. The percent inhibition of AVP-induced aggregation was measured and an IC$_{50}$ calculated.

In studies using washed platelets, 50 mL of whole blood was mixed with 10 mL of citrate/heparin solution (85 mM sodium citrate, 64 mM citric acid, 111 mM glucose, 5 units/mL heparin) and PRP isolated as described above. PRP was then centrifuged (150×g) and the pellet resuspended in a physiologic buffer solution (10 mM HEPES, 135 mM sodium chloride, 5 mM potassium chloride, and 1 mM magnesium chloride) containing 10 μM indomethicin. Human fibrinogen (0.2 mg/mL) and calcium chloride (1 mM) were added to stirred platelets before initiating aggregation with AVP (30 nM) as previously described.

Method Example 16

Flank marking behavior in golden hamsters. Obsessive-compulsive disease appears in a great variety of degrees and symptoms, generally linked by the victim's uncontrollable urge to perform needless, ritualistic acts. Acts of acquiring, ordering, cleansing and the like, beyond any rational need or rationale, are the outward characteristic of the disease. A badly afflicted subject may be unable to do anything but carry out the rituals required by the disease. Obsessive-compulsive disease, in all its variations, is a preferred target of treatment with the present adjunctive therapy method and compositions. The utility of the compounds of Formula (I) in the treatment of obsessive-compulsive disorder was demonstrated as described in the following assay.

In golden hamsters, a particular stereotypy, flank marking behavior, can be induced by microinjections of vasopressin (10-100 nL, 1-100 μM) into the anterior hypothalamus (Ferris et al., *Science*, 224, 521-523 (1984); Albers and Ferris, *Regulatory Peptides*, 12, 257-260 (1985); Ferris et al., *European Journal of Pharmacology*, 154, 153-159 (1988)). Following the releasing stimulus, the behavior is initiated by grooming, licking and combing of the large sebaceous glands on the dorsolateral flanks. Bouts of flank gland grooming may be so intense that the flank region is left matted and soaked in saliva. After grooming, the hamsters display flank marking behavior, a type of scent marking involved in olfactory communication (Johnston, *Physio. Behav.*, 51, 437-448 (1985); Ferris et al., *Physio. Behav.*, 40, 661-664 (1987)), by arching the back and rubbing the flank glands vigorously against any vertical surface. Vasopressin-induced flank marking is usually induced within a minute after the microinjection (Ferris et al., *Science*, 224, 521-523 (1984)). The behavior is specific to vasopressin, as micro-injections of other neuropeptides, excitatory amino acids, and catecholamines do not elicit flank marking (Ferris et al., *Science*, 224, 521-523 (1984); Albers and Ferris, *Regulatory Peptides*, 12, 257-260 (1985)). Furthermore, flank marking is specific to the vasopressin $V_1$ receptor, as the behavior is selectively inhibited by $V_1$ receptor antagonists and activated by $V_1$ receptor agonists (Ferris et al., *Neuroscience Letters*, 55, 239-243 (1985); Albers et al., *Journal of Neuroscience*, 6, 2085-2089 (1986); Ferris et al., *European Journal of Pharmacology*, 154, 153-159 (1988)).

All animals in this assay are adult male golden hamsters (*Mesocricetus auratus*) weighing approximately 160 gm. The animals undergo stereotaxic surgery, and are allowed to recover before behavioral testing. The hamsters are kept on a reverse light cycle (14 hr light, 10 hr dark, lights on at 19:00) in Plexiglas™ cages, and receive food and water ad libitum.

Stereotaxic surgery is performed under pentobarbital anesthesia. The stereotaxic coordinates are: 1.1 mm anterior to the bregma, 1.8 mm lateral to the midsagittal suture at an 8° angle from the verticle line, and 4.5 mm below the dura. The nose bar is placed at the level of the interaural line. An unilateral 26-gauge guide cannula is lowered to the site and secured to the skull with dental cement. The guide cannulae are closed with a 33-gauge obturator extending 1 mm beyond the guide. The innercanulae used for the microinjections extends 3.0 mm beyond the guide to reach the anterior hypothalamus.

The hamsters are microinjected with 1 μM vasopressin in a volume of 150 nL. The vasopressin is given as a cocktail with 200 mM, 20 mM, 2 mM of the test compound or alone, in the vehicle, dimethylsulfoxide. Both the vasopressin and the test compound are dissolved in 100% dimethylsulfoxide. All injections are aimed at the anterior hypothalamus. Animals are scored for flank marking for a period of 10 minutes in a clean cage.

Method Example 17

Use in combination with a serotonin reuptake inhibitor. Another aspect of this invention is the use of compounds of Formula (I) in combination with a serotonin reuptake inhibitor for use in the treatment of obsessive-compulsive disease, aggressive disorder, or depression. Compounds useful as serotonin reuptake inhibitors include but are not limited to:

Fluoxetine, N-methyl-3-(p-trifluoromethylphenoxy)-3-phenylpropylamine, is marketed in the hydrochloride salt form, and as the racemic mixture of its two enantiomers. U.S. Pat. No. 4,314,081 is an early reference on the compound. Robertson et al., *J. Med. Chem.*, 31, 1412 (1988), taught the separation of the R and S enantiomers of fluoxetine and showed that their activity as serotonin uptake inhibitors is similar to each other. In this document, the word "fluoxetine" will be used to mean any acid addition salt or the free base, and to include either the racemic mixture or either of the R and S enantiomers;

Duloxetine, N-methyl-3-(1-naphthalenyloxy)-3-(2-thienyl)propanamine, is usually administered as the hydrochloride salt and as the (+) enantiomer. It was first taught by U.S. Pat. No. 4,956,388, which shows its high potency. The word "duloxetine" will be used here to refer to any acid addition salt or the free base of the molecule;

Venlafaxine is known in the literature, and its method of synthesis and its activity as an inhibitor of serotonin and norepinephrine uptake are taught by U.S. Pat. No. 4,761,501. Venlafaxine is identified as compound A in that patent;

Milnacipran (N,N-diethyl-2-aminomethyl-1-phenylcyclopropanecarboxamide) is taught by U.S. Pat. No. 4,478,836, which prepared milnacipran as its Example 4. The patent describes its compounds as antidepressants. Moret et al., *Neuropharmacology*, 24, 1211-19 (1985), describe its pharmacological activities as an inhibitor of serotonin and norepinephrine reuptake;

Citalopram, 1-[3-(dimethylamino)propyl]-1-(4-fluorophenyl)-1,3-dihydro-5-isobenzofurancarbonitrile, is disclosed in U.S. Pat. No. 4,136,193 as a serotonin reuptake inhibitor. Its pharmacology was disclosed by Christensen et al., *Eur. J. Pharmacol.*, 41, 153 (1977), and reports of its clinical effectiveness in depression may be found in Dufour et al., *Int. Clin. Psychopharmacol.*, 2, 225 (1987), and Timmerman et al., ibid., 239;

Fluvoxamine, 5-methoxy-1-[4-(trifluoromethyl)phenyl]-1-pentanone O-(2-aminoethyl)oxime, is taught by U.S. Pat. No. 4,085,225. Scientific articles about the drug have been published by Claassen et al., *Brit. J. Pharmacol.*, 60, 505 (1977); and De Wilde et al., *J. Affective Disord.*, 4, 249 (1982); and Benfield et al., *Drugs*, 32, 313 (1986);

Paroxetine, trans-(−)-3-[(1,3-benzodioxol-5-yloxy)methyl]-4-(4-fluorophenyl)piperidine, may be found in U.S. Pat. Nos. 3,912,743 and 4,007,196. Reports of the drug's activity are in Lassen, *Eur. J. Pharmacol.*, 47, 351 (1978); Hassan et al., *Brit. J. Clin. Pharmacol.*, 19, 705 (1985); Laursen et al., *Acta Psychiat. Scand.*, 71, 249 (1985); and Battegay et al., *Neuropsychobiology*, 13, 31 (1985); and Sertraline, (1S-cis)-4-(3,4-dichlorophenyl)-1,2,3,4-tetrahydro-N-methyl-1-naphthylamine hydrochloride, a serotonin reuptake inhibitor disclosed in U.S. Pat. No. 4,536,518, is marketed as an antidepressant.

All of the above-referenced patents are hereby incorporated by reference.

The adjunctive therapy of this aspect of the present invention is carried out by administering a vasopressin $V_{1a}$ antagonist described herein together with a serotonin reuptake inhibitor in any manner that provides effective levels of the compounds in the body at the same time. All of the compounds concerned are orally available and are normally administered orally, and so oral administration of the adjunctive combination is preferred. They may be administered together, in a single dosage form, or may be administered separately.

This aspect of the present invention provides a potentiation of the decrease in the concentration of vasopressin observed as an effect of administration of a vasopressin $V_{1a}$ antagonist by administration of a serotonin reuptake inhibitor. This aspect of the present invention is particularly suited for use in the treatment of depression and obsessive compulsive disorder. Such disorders may often be resistant to treatment with a serotonin reuptake inhibitor alone.

While it is possible to administer a compound employed in the methods described herein directly without any formulation, the compounds are usually administered in the form of pharmaceutical compositions comprising a pharmaceutically acceptable excipient and at least one active ingredient. These compositions can be administered by a variety of routes including oral, rectal, transdermal, subcutaneous, intravenous, intramuscular, and intranasal. Many of the compounds employed in the methods described herein are effective as both injectable and oral compositions. Such compositions are prepared in a manner well known in the pharmaceutical art and comprise at least one active compound. See, e.g., REMINGTON'S PHARMACEUTICAL SCIENCES, (16th ed. 1980).

In making the pharmaceutical compositions used in the methods described herein, the active ingredient is usually mixed with an excipient, diluted by an excipient, or enclosed within such a carrier which can be in the form of a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions described herein can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For example, dosages per day normally fall within the range from about 0.01 to about 30 mg/kg of body weight. In illustrative variations, dosages per day may fall in the range from about 0.02 to about 10 mg/kg of body weight, in the range from about 0.02 to about 1 mg/kg of body weight, or in the range from about 0.02 to about 0.1 mg/kg of body weight. Such dosage ranges are applicable for the treatment of any patient or mammal. In addition, for the treatment of adult humans, illustrative doses fall in the range from about 0.02 to about 15 mg/kg of body weight, or in the range from about 0.1 to about 10 mg/kg/day, in single or divided dose. However, it is to be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are intended to be illustrative are not intended to and should not be interpreted to limit the invention in any way. In some instances dosage levels below the lower limit of the aforesaid range may be more than adequate, while in other cases still larger doses may be employed without causing any harmful side effect. It is appreciated that such larger doses may be first divided into several smaller doses for administration throughout the day.

The type of formulation employed for the administration of the compounds employed in the methods described herein may be dictated by the particular compounds employed, the type of pharmacokinetic profile desired from the route of administration and the compound(s), and the state of the patient.

Formulation Example 1

Hard gelatin capsules containing the following ingredients are prepared:

| Ingredient | Quantity (mg/capsule) |
| --- | --- |
| Compound of formula (I) | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
| --- | --- |
| Compound of formula (I) | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
| --- | --- |
| Compound of formula (I) | 5 |
| Lactose | 95 |

The active mixture is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
| --- | --- |
| Compound of formula (I) | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch, and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50-60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
| --- | --- |
| Compound of formula (I) | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Quantity (mg) |
| --- | --- |
| Compound of formula (I) | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Quantity (mg) |
| --- | --- |
| Compound of formula (I) | 50.0 mg |
| Xanthan gum | 4.0 mg |
| Sodium carboxymethyl cellulose(11%) Macrocrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose, and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

Capsules, each containing 15 mg of medicament, are made as follows:

| Ingredient | Quantity (mg/capsule) |
| --- | --- |
| Compound of formula (I) | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Example 9

An intravenous formulation may be prepared as follows:

| Ingredient | Quantity (mg) |
| --- | --- |
| Compound of formula (I) | 250.0 mg |
| Isotonic saline | 1000 ml |

Formulation Example 10

A topical formulation may be prepared as follows:

| Ingredient | Quantity (mg) |
| --- | --- |
| Compound of formula (I) | 1-10 g |
| Emulsifying Wax | 30 g |
| Liquid Paraffin | 20 g |
| White Soft Paraffin to | 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

Sublingual or buccal tablets, each containing 10 mg of active ingredient, may be prepared as follows:

| Ingredient | Quantity (mg/tablet) |
| --- | --- |
| Compound of formula (I) | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the resulting solution is cooled to about 50-55° C. and the medicament is slowly admixed. The homogenous mixture is poured into forms made of an inert material to produce a drug-containing diffusion matrix having a thickness of about 2-4 mm. This diffusion matrix is then cut to form individual tablets having the appropriate size.

Formulation Example 12

In the methods described herein, another illustrative formulation employs transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Formulation Example 13

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, which is herein incorporated by reference.

Formulation Example 14

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions that can transiently open the blood-brain barrier.

While the invention has been illustrated and described in detail in the foregoing description, such an illustration and description is to be considered as illustrative and exemplary and not restrictive in character, it being understood that only the illustrative embodiments have been shown and described and that all changes and modifications that come within the spirit of the invention are desired to be protected.

What is claimed is:

1. A compound of the formula

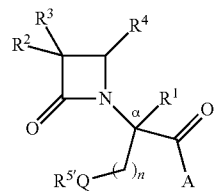

or a pharmaceutically acceptable salt thereof, wherein:
Q is sulfur;
n is 1 or 2;
A is an optionally substituted (arylalkyl)amino or an optionally substituted nitrogen-containing heterocycle attached at a nitrogen;
$R^1$ is hydrogen;
$R^2$ is hydrogen;
$R^3$ is

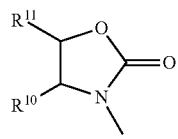

wherein $R^{10}$ optionally substituted alkyl, optionally substituted cycloalkyl, or optionally substituted aryl; and $R^{11}$ is hydrogen;
$R^4$ is optionally substituted arylalkyl, optionally substituted arylalkenyl, or optionally substituted arylalkynyl; and
$R^{5'}$ is $C_1$-$C_6$ alkyl, $C_3$-$C_8$ cycloalkyl, or optionally-substituted arylalkyl.

2. The compound of claim 1 wherein n is 1.
3. The compound of claim 1 wherein n is 2.
4. The compound of claim 1 wherein A is an optionally substituted (arylalkyl)amino.
5. The compound of claim 1 wherein A is an optionally substituted nitrogen-containing heterocycle attached at a nitrogen.
6. The compound of claim 1 wherein the heterocycle is pyrrolidinyl, piperidinyl, or piperazinyl.
7. The compound of claim 1 wherein A is piperidinyl or piperazinyl, each of which is substituted at the 4-position with pyrrolidinyl, piperidinyl, piperazinyl, homopiperazinyl, pyrrolidinyl($C_1$-$C_4$ alkyl), piperidinyl($C_1$-$C_4$ alkyl), piperazinyl ($C_1$-$C_4$ alkyl), or homopiperazinyl($C_1$-$C_4$ alkyl).
8. The compound of claim 1 wherein A is piperidinylpiperidinyl or piperidinylalkylpiperidinyl.
9. The compound of claim 1 wherein $R^{10}$ is alkyl, cycloalkyl, or aryl.
10. The compound of claim 1 wherein $R^{10}$ is aryl.
11. The compound of claim 1 wherein $R^4$ is optionally substituted arylethyl, optionally substituted arylethenyl, or optionally substituted arylethynyl.
12. The compound of claim 1 wherein $R^4$ is optionally substituted phenylethenyl.
13. The compound of claim 1 wherein $R^4$ is phenylethenyl.
14. The compound of claim 1 wherein $R^{5'}$ is optionally-substituted arylalkyl.
15. The compound of claim 1 wherein $R^{5'}$ is arylalkyl.
16. The compound of claim 1 wherein $R^{5'}$ is optionally-substituted benzyl.
17. The compound of claim 1 wherein $R^{5'}$ is benzyl.
18. The compound of claim 1 of the formula

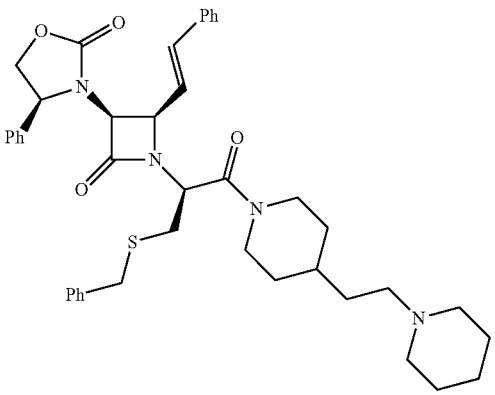 [SMILES: O=C([C@@H](CSCc1ccccc1)N1C(=O)[C@@H](N2C(=O)OC[C@@H]2c2ccccc2)[C@H]1/C=C/c1ccccc1)N1CCC(CCN2CCCCC2)CC1]

or a pharmaceutically acceptable salt thereof.
19. A pharmaceutical composition comprising one or more compounds of claim 1 and one or more pharmaceutically acceptable carriers, diluents, or excipients, or a combination thereof.

* * * * *